United States Patent
Joly et al.

(10) Patent No.: US 10,758,573 B2
(45) Date of Patent: Sep. 1, 2020

(54) COMPOSITIONS AND METHODS FOR ENRICHMENT OF CELLS

(71) Applicants: President and Fellows of Harvard College, Cambridge, MA (US); CHARITÉ UNIVERSITÄTSMEDIZIN BERLIN, Berlin (DE)

(72) Inventors: Pascal Joly, Boston, MA (US); Georg N. Duda, Berlin (DE); Thomas Schaus, Boston, MA (US); Anke Dienelt, Berlin (DE); Andrea Sass, Berlin (DE); David J. Mooney, Sudbury, MA (US)

(73) Assignees: President and Fellows of Harvard College, Cambridge, MA (US); CHARITÉUNIVERSITÄTSMEDIZIN BERLIN, Berlin (DE)

( * ) Notice: Subject to any disclaimer, the term of this patent is extended or adjusted under 35 U.S.C. 154(b) by 67 days.

(21) Appl. No.: 15/580,710

(22) PCT Filed: Jun. 9, 2016

(86) PCT No.: PCT/US2016/036742
§ 371 (c)(1),
(2) Date: Dec. 8, 2017

(87) PCT Pub. No.: WO2016/201129
PCT Pub. Date: Dec. 15, 2016

(65) Prior Publication Data
US 2018/0185417 A1    Jul. 5, 2018

Related U.S. Application Data

(60) Provisional application No. 62/173,109, filed on Jun. 9, 2015.

(51) Int. Cl.
| | |
|---|---|
| *A61K 35/32* | (2015.01) |
| *C12N 5/078* | (2010.01) |
| *A61K 35/12* | (2015.01) |
| *C07K 14/705* | (2006.01) |
| *C12N 15/115* | (2010.01) |

(52) U.S. Cl.
CPC .............. *A61K 35/32* (2013.01); *A61K 35/12* (2013.01); *C07K 14/70596* (2013.01); *C12N 5/0634* (2013.01); *C12N 15/115* (2013.01); *C12N 2310/16* (2013.01); *C12N 2310/3517* (2013.01)

(58) Field of Classification Search
None
See application file for complete search history.

(56) References Cited

U.S. PATENT DOCUMENTS

| | | | |
|---|---|---|---|
| 6,635,469 B1 * | 10/2003 | Litt | B01J 3/00 435/287.1 |
| 2014/0314869 A1 | 10/2014 | Caplan | |
| 2014/0315295 A1 * | 10/2014 | Makarova | G01N 1/34 435/325 |
| 2015/0079677 A1 | 3/2015 | Yamanishi et al. | |
| 2016/0003835 A1 * | 1/2016 | Halbert | G01N 33/57492 506/9 |
| 2016/0223441 A1 * | 8/2016 | Gjerde | C12N 1/02 |

FOREIGN PATENT DOCUMENTS

WO   WO-2014068408 A2   5/2014

OTHER PUBLICATIONS

Hasegawa et al., Molecules, 21(421):1-15 (2016) (Year: 2016).*
BD, Cell Marker Handbook (2010) (Year: 2010).*
Cancer Nanotech., Humana Press (2010) (Year: 2010).*
Cell Separation, Springer (2007) (Year: 2007).*
Guo et al., Stem Cells, 24:2220-2231 (2006) (Year: 2006).*
Herr et al., Anal. Chem., 78:2918-2924 (2006) (Year: 2006).*
Hoffmann et al., J. Biomed. Mater. Res., 84A:614-621 (2008) (Year: 2008).*
Methods Mol. Biol., 3rd Ed. 1286, Humana Press (2015) (Year: 2015).*
Pan et al., Biosens. Bioelect., 25:1609-1614 (2010) (Year: 2010).*
Porschewski et al., J. Biomol. Screening, 11(7):773-781 (2006) (Year: 2006).*
Shao et al., Chem. Commun., 48:6684-6686 (2012) (Year: 2012).*
Smith et al., Anal. Chem., 79:3075-3082 (2007) (Year: 2007).*
Wan et al., Cancer Res; 70(22):9371-9380 (2010) (Year: 2010).*
Wan et al., Lab Chip, 12(22):4693-4701 (2012) (Year: 2012).*
Zhang et al., Anal. Methods, 7:6339-6345 (2015) (Year: 2015).*
Zhao et al., Trends Anal. Chem., 41:46-57 (2012) (Year: 2012).*
Zhu et al., Lab Chip, 12:3504-3513 (2012) (Year: 2012).*
Wan et al., "Capture, isolation and release of cancer cells with aptamer-functionalized glass bead array", Lab Chip, Jan. 2012, vol. 12, pp. 4693-4701.
Zheng et al. "Cell detachment: Post-isolation challenges", Biotechnology Advances, vol. 31, Issue 8, Dec. 2013, pp. 1664-1675.
Citartan et al., "Aptamers as the 'capturing' agents in aptamer-based capture assays", Microchemical Journal vol. 128, Sep. 2016, pp. 187-197.

(Continued)

*Primary Examiner* — Thomas J. Visone
(74) *Attorney, Agent, or Firm* — McCarter & English, LLP; Maria Laccotripe Zacharakis; Deborah L. Nagle

(57) ABSTRACT

The present invention is directed to a device for enriching cells with a cell surface marker, comprising an aptamer suitable for specifically binding the cell surface marker, and beads coupled thereto, wherein the aptamer is coupled to the beads in a manner that allows for release of cells expressing the cell surface marker, in the absence of a chemical agent, and production of a cell population enriched for cells expressing the cell surface marker, substantially free of beads and aptamer. Kits comprising the device or components thereof, and methods of cell enrichment, are also provided. In exemplary embodiments, the device contains an aptamer that specifically binds CD31.

29 Claims, 16 Drawing Sheets

Specification includes a Sequence Listing.

(56) References Cited

OTHER PUBLICATIONS

Zhu et al., "Spatially selective release of aptamer-captured cells by temperature mediation", IET Nanobiotechnol. Mar. 2014; 8(1): 2-9.

* cited by examiner

Incorporation of aptamer
in traditional magnetic separation

Tissue

Liquid

COMPOSITIONS AND METHODS FOR ENRICHMENT OF CELLS

RELATED APPLICATIONS

This application is a 35 U.S.C. § 371 national stage filing of International Application No. PCT/US2016/036742, filed on Jun. 9, 2016, which in turn claims the benefit of priority to U.S. Provisional Application No. 62/173,109, filed on Jun. 9, 2015. The entire contents of each of the foregoing applications are incorporated herein by reference.

BACKGROUND OF THE INVENTION

In order for cell therapies to be translated from the bench to the clinic, they must follow good manufacturing practice guidelines and be approved by regulatory agencies. In the case of exogenous cell therapies, significant regulatory constraints on cell isolation and in vitro expansion procedures to ensure the quality and safety of the resultant product lead to high costs (Li et al., *Expert opinion on biological therapy.* 2015; 15(9):1293-306; Riis et al., *Expert Rev Mol Med.* 2015; 17: e11). An alternative approach is to use endogenous cells, obtained from the subject to be treated. Approaches have been developed to obtain a sufficient number of cells for therapy, such as cytokine-based cell mobilization, e.g., the use of granulocyte colony-stimulating factor for the mobilization of hematopoietic stem cells (Griese et al., *Circulation.* 2003;108: 2710-2715). However, not only does this approach necessitate several visits to the hospital for injections or to collect cells, but it is also associated with a wide variety of side-effects ranging from flu-like symptoms to more severe conditions (Ozkan et al., *Transfus Apher Sci.* 2015; 3(1):13-6).

In contrast, intraoperative cell therapies, in which cells are harvested from a patient prior to or during an operation, and then are re-administered, often during the same surgical session, represent a new class of exciting approaches that hold promise to overcome the high costs and many of the potential drawbacks associated with ex vivo cell expansion and cytokine-based cell mobilization. Such intraoperative approaches have the potential to save time and reduce costs for both patients and clinicians (FIG. 1).

However, current approaches for positive cell isolation usually employ magnetic beads for separation, for examples, magnetic beads that are coupled with high-affinity antibodies. These beads remain attached to the cells that are to be transplanted. Although magnetic bead and/or antibody-based cell separation approaches are useful for selection of cells in a laboratory setting, they are not ideal for isolation of cells for administration to a subject (e.g., cell therapy) because of the presence of contaminants in the isolated cell population, including residual antibody, residual beads, and/or chemical agents. In both Europe and the USA, modification of transplanted cells, including the use of antibodies or antibody-labeled beads that are not removed, may constitute more than a minimal manipulation. The resulting cells could consequently be classified as an advanced-therapy medicinal product (ATMP), resulting in substantially greater regulatory burden. Accordingly, new approaches for cell isolation are needed.

SUMMARY OF THE INVENTION

The present invention is based, at least in part, on the development of devices and methods for enriching and/or isolating cells with a specific cell surface marker, e.g., CD31+ cells, that are substantially free from contamination. In embodiments, the devices and methods employ an aptamer that specifically binds a cell surface marker, e.g., CD31. Thus, the invention includes methods and compositions for enriching cells with a cell surface marker, e.g., CD31+ cells, to obtain an enriched cell population, e.g., a CD31+ cell population, that is substantially free of beads, aptamer, or any other undesired contaminants. Such an enriched cell population, e.g., CD31+ cell population, is suitable for direct administration to a subject. Accordingly, in a further embodiment, the invention includes methods and compositions for cell-based therapy using enriched populations of cells, e.g., CD31+ cells. For example, CD31+ cells can be used therapeutically to promote angiogenesis and/or osteogenesis, e.g., at a surgical site in a subject.

One aspect of the invention provides a device for enriching cells with a cell surface marker, comprising an aptamer suitable for specifically binding the cell surface marker; and beads having a diameter of about 30-200 µm; wherein the aptamer is coupled to the beads in a manner that allows for release of the cells in the absence of a chemical agent, and production of a cell population enriched for cells with the cell surface marker substantially free of beads and aptamer.

In one embodiment, the cell surface marker is selected from the group consisting of CD31, T-cell receptor (TCR), CD2, CD3, CD5, CD4, CD8, complement receptors, Fc receptors, MHC Class II molecules, membrane immunoglobulin, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and combinations thereof. In another embodiment, the cell surface marker is CD31.

In one embodiment of the invention, the beads are packed in a column. The column optionally comprises a filter. In preferred embodiments, the filter has a pore size smaller than the diameter of the beads.

In one embodiment, the aptamer is non-covalently coupled to the beads. In another embodiment, the aptamer is biotinylated, and the beads are coupled to streptavidin, NeutrAvidin, etc. In an alternative embodiment, the aptamer is coupled to streptavidin, NeutrAvidin, etc., and the beads are biotinylated. In these embodiments, the aptamer is coupled to the beads through the interaction of biotin and streptavidin. In another embodiment, the aptamer is covalently coupled to the beads.

In one embodiment, the beads are agarose beads. In another embodiment, the beads are not magnetic. In one embodiment, the beads have a diameter of about 50-150 µm. In another embodiment, the beads have a diameter of about 100-150 µm.

In one embodiment, the aptamer is present at a concentration of about 1-20 µg/mL of beads. In another embodiment, the aptamer is present at a concentration of about 5 µg/mL of beads.

In one embodiment, the device further comprises beads having a diameter of about 30-200 µm that are not coupled to the aptamer. In one embodiment, the beads coupled to the aptamer and the beads not coupled to the aptamer are present in a ratio of about 1:1 to about 3:1. In another embodiment, the column is sized to fit inside a centrifuge tube. In yet another embodiment, the column is fitted with a syringe.

Another aspect of the invention provides a method of enriching cells with a cell surface marker in a cell population, comprising providing aptamer-coupled beads having a diameter of about 30-200 μm, wherein the aptamer is suitable for specifically binding the cell surface marker; contacting the aptamer-coupled beads with the cell population containing cells with and without the cell surface marker; washing the aptamer-coupled beads with a wash buffer such that all or a portion of the cells without the cell surface marker are removed from the cell sample; subjecting the aptamer-coupled beads to a mechanical force sufficient to release the cells with the cell surface marker from the aptamer-coupled beads; and recovering the cells with the cell surface marker from the aptamer-coupled beads; thereby producing a cell population that is enriched in cells with the cell surface marker and is substantially free of beads and/or aptamer.

In one embodiment, the cell surface marker is selected from the group consisting of CD31, T-cell receptor (TCR), CD2, CD3, CD5, CD4, CD8, complement receptors, Fc receptors, MHC Class II molecules, membrane immunoglobulin, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and combinations thereof. In another embodiment, the cell surface marker is CD31.

In one embodiment, the mechanical force is applied by resuspension of the aptamer-coupled beads in a resuspension buffer, wherein the resuspension buffer does not contain an agent capable of releasing the cells with the cell surface marker from the aptamer-coupled beads, for example, a chemical agent or a nuclease. In yet another embodiment, the resuspension buffer is phosphate buffered saline (PBS). In one embodiment, the mechanical force is applied by shaking, pipetting, or vortexing the aptamer-coupled beads. In another embodiment, the cells with the cell surface marker are recovered from the aptamer-coupled beads by passage through a filter having a pore size of less than 30 μm. In an alternative embodiment, the cells with the cell surface marker are recovered from the aptamer-coupled beads by centrifugation. In one embodiment, the method is performed in the absence of an antibody specific for the cell surface marker. In another embodiment, the beads are not magnetic.

In one embodiment, the cell population is isolated from a blood sample, a bone marrow sample, a hematoma sample, a tissue sample collected at the site of a bone fracture, a fluid sample collected at the site of a bone fracture, or combinations thereof. In another embodiment, the cell population is isolated from a peripheral blood mononuclear cell (PBMC) sample. In a further embodiment, the cell population is isolated from a tissue sample collected at the site of a bone fracture or a fluid sample collected at the site of a bone fracture.

In a further embodiment, the method further comprises obtaining the cell sample from a subject. In yet another embodiment, the method further comprises administering the cell population enriched for cells with the cell surface marker to a subject. In one embodiment, the cell population enriched for cells with the cell surface marker is administered to the subject by introduction at a surgical site. In another embodiment, the cell population enriched for cells with the cell surface marker is administered to the subject by injection. In an exemplary embodiment, the cell population is administered to the subject by injection at the site of a bone fracture.

One aspect of the invention provides a cell population enriched for cells with a cell surface marker and substantially free of beads and/or aptamer, obtainable by the methods described herein.

In one embodiment, the cell surface marker is selected from the group consisting of CD31, T-cell receptor (TCR), CD2, CD3, CD5, CD4, CD8, complement receptors, Fc receptors, MHC Class II molecules, membrane immunoglobulin, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and combinations thereof. In another embodiment, the cell surface marker is CD31.

Another aspect of the invention provides a cell population enriched for CD31+ cells and substantially free of beads and/or aptamer, obtainable by the methods described herein.

One aspect of the invention provides a method of promoting angiogenesis and/or osteogenesis at a surgical site in a subject. In embodiments, this aspect comprises obtaining a cell sample from the subject, wherein the cell sample contains CD31+ and CD31– cells; contacting the cell sample with aptamer-coupled beads having a diameter of about 30-200 iLim, wherein the aptamer is suitable for specifically binding CD31; washing the aptamer-coupled beads with a wash buffer such that all or a portion of the CD31-cells are removed from the cell sample; subjecting the aptamer-coupled beads to a mechanical force sufficient to release the CD31+ cells from the aptamer-coupled beads; recovering the CD31+ cells from the aptamer-coupled beads; such that the recovered CD31+ cells are substantially free of beads and/or aptamer, and introducing the recovered CD31+ cells at the surgical site in the subject.

In one embodiment, the surgical site is a bone fracture site. In another embodiment, the method is performed intraoperatively. In yet another embodiment, the method can be performed in 30 minutes or less.

Another aspect of the invention provides a kit for enrichment of cells expressing a cell surface marker from a subject. In embodiments of this aspect, the kits can include a portable column packed with aptamer-coupled beads having a diameter of about 30-200 μm, wherein the aptamer is suitable for specifically binding the cell surface marker, and wherein the column comprises a filter having a pore size smaller than the diameter of the beads. Kits of the invention can optionally include instructions for use of the kit to enrich cells with the cell surface marker from a subject cell sample comprising cells with and without the cell surface marker. In embodiments, portable columns included with the kits of the invention are prepackaged in a sterile container.

In one embodiment, the cell surface marker is selected from the group consisting of CD31, T-cell receptor (TCR), CD2, CD3, CD5, CD4, CD8, complement receptors, Fc receptors, MHC Class II molecules, membrane immunoglobulin, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and combinations thereof. In another embodiment, the cell surface marker is CD31.

In an illustrative embodiment, a blood sample is collected while the patient is being prepared for surgery, or just after anesthesia. Other sources such as bone marrow, hematoma or tissue waste can also be collected intraoperatively. In parallel to the surgeon accessing the injury location (e.g. bone fracture), a specific cell population from the sample is the target of enrichment. A general outline is illustrated using CD31+ cells as an example. The desired fraction is then ready to be administered to the patient to promote a regenerative process. The duration of the enrichment procedure should approximately coincide with the time required to perform the surgical procedure, e.g., the time required to access the location of the injury.

Figure 1:
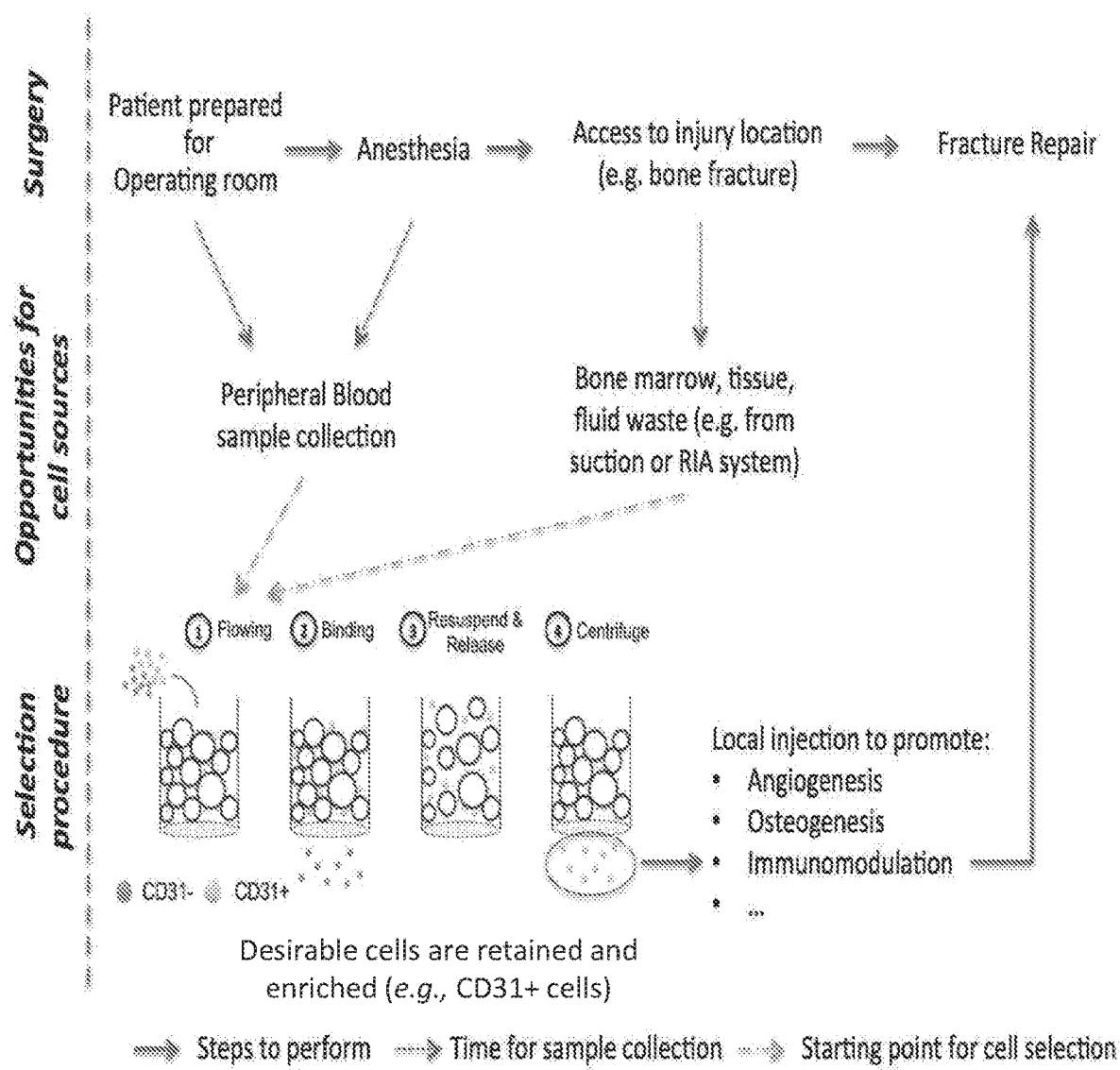
FIG. 1 depicts the general concept for intraoperative cell therapies and applications thereof for treating bone fracture.
Figure 2A:
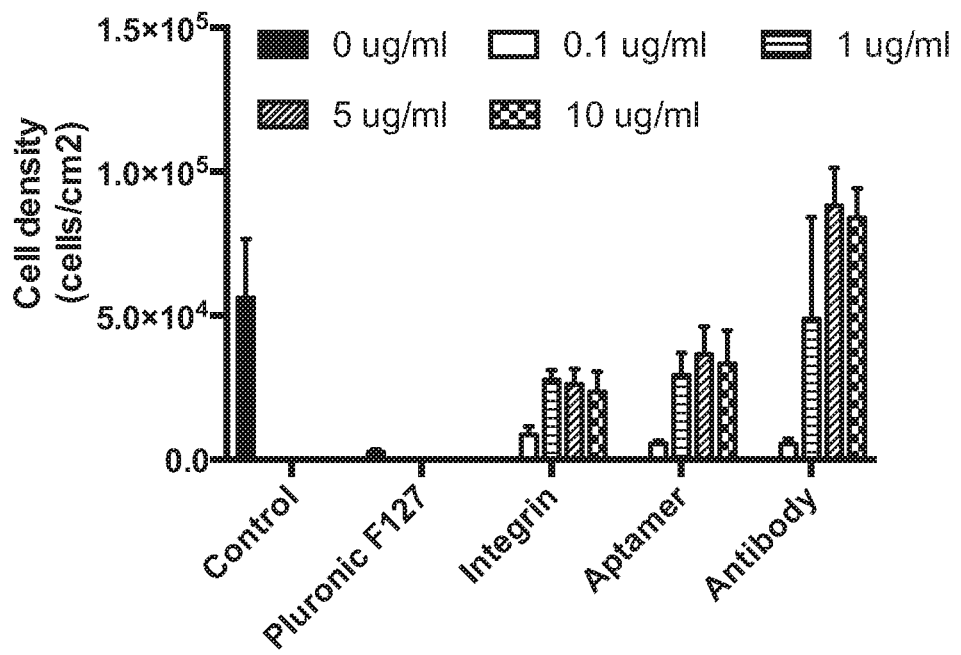
Figure 2B:
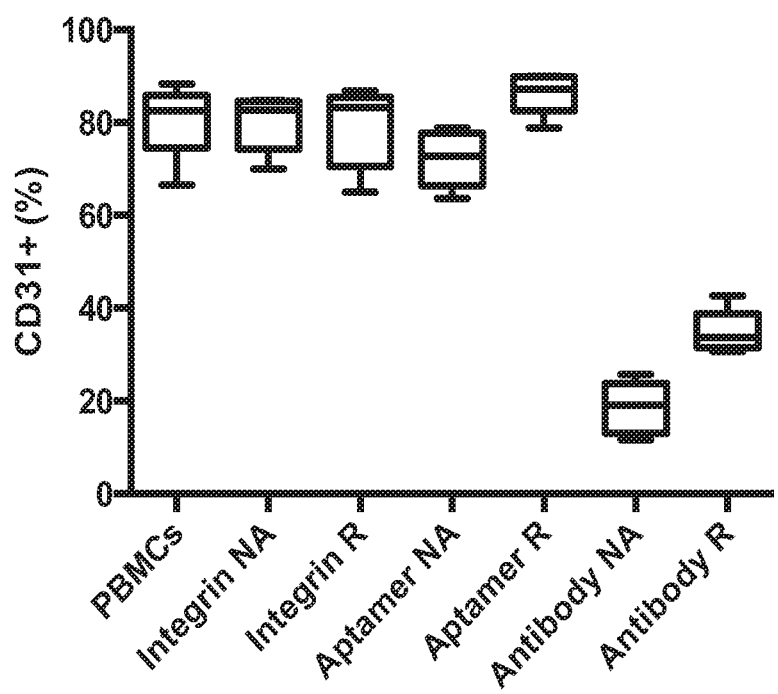
Figure 2C:
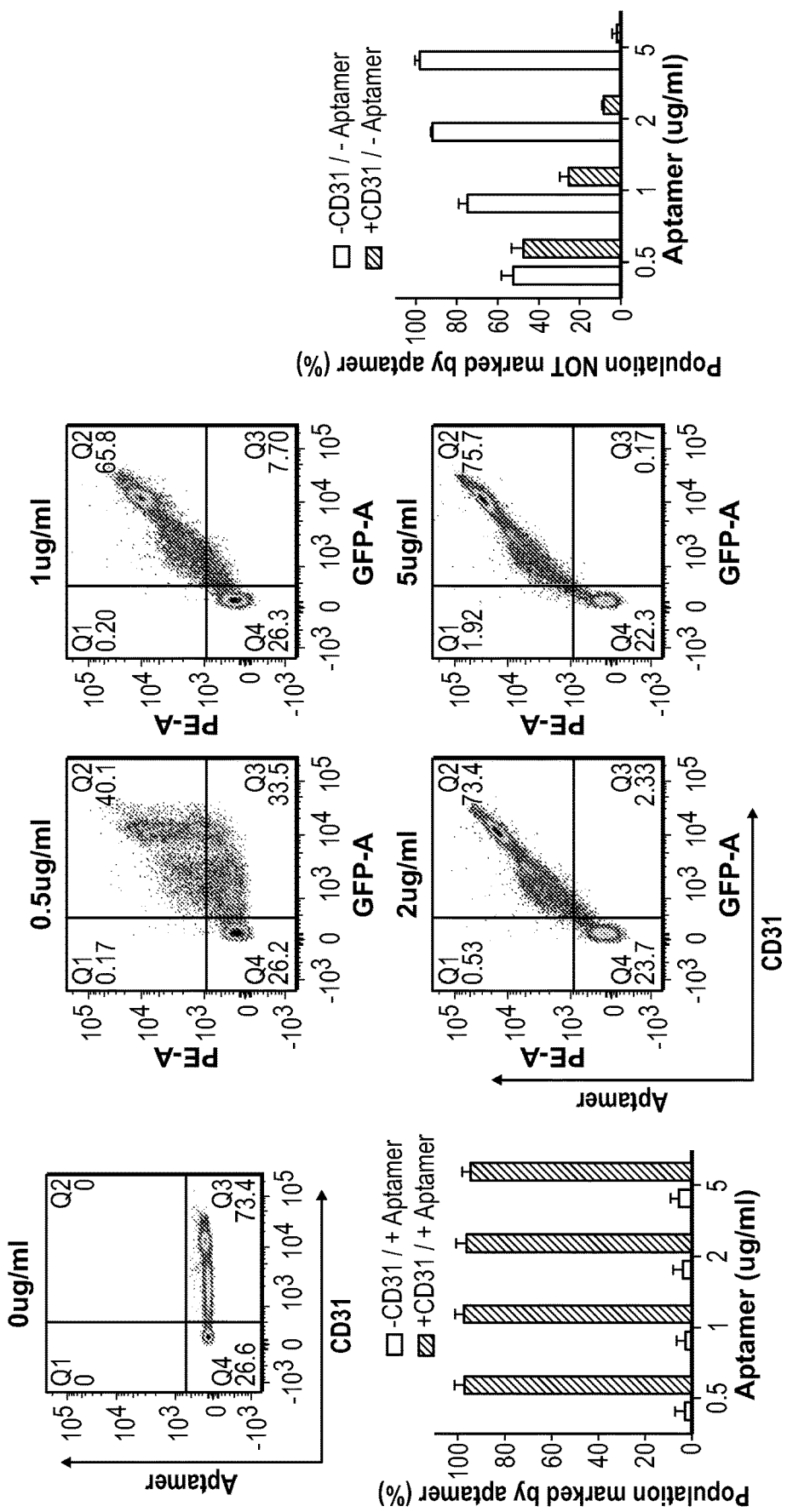
Figure 2D:
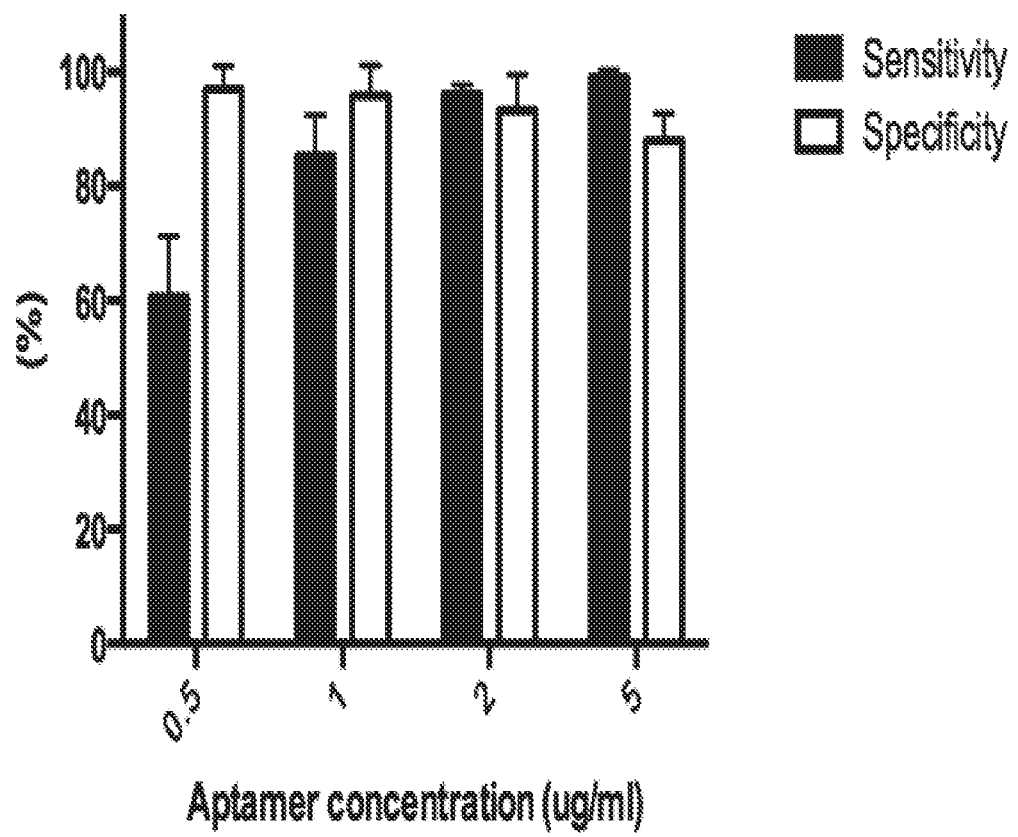
Figure 2E:
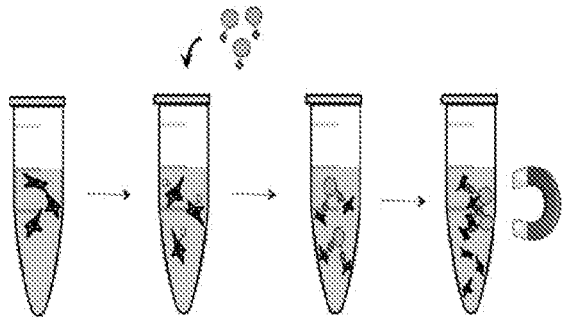
Figure 2E:
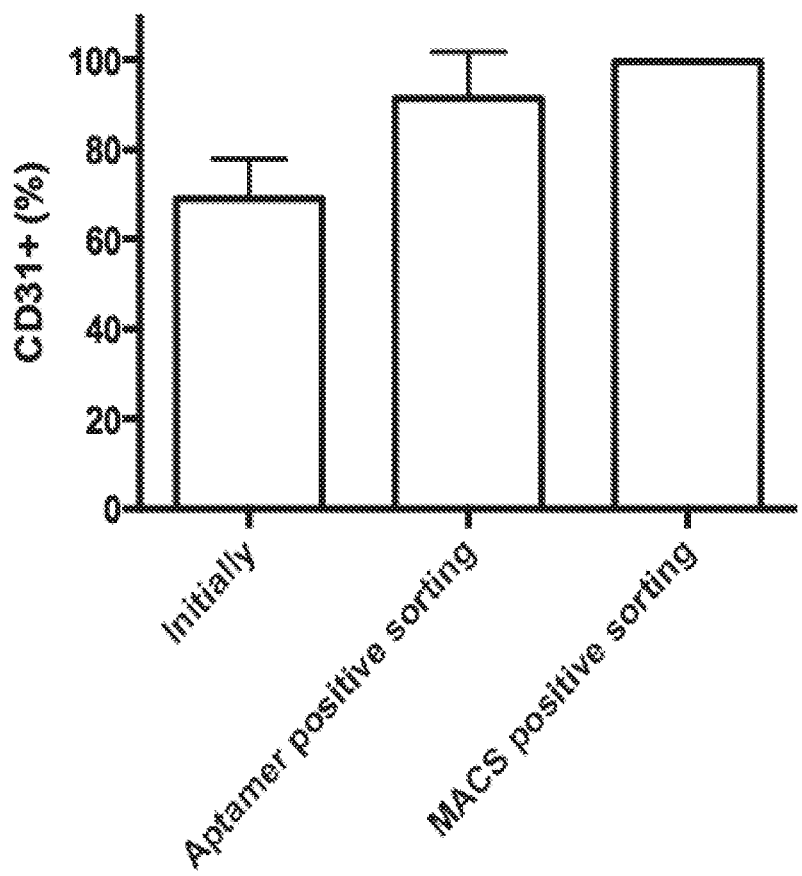

FIGS. 2A-2D depict the selection and validation of a CD31 aptamer for cell isolation. Specifically, FIG. 2A depicts the ligand capacity to capture cells among peripheral blood mononuclear cells (PBMCs) during 2D cell adhesion assays. FIG. 2B depicts the purity of CD31+ cells captured during the adhesion assay and the potential for mechanical release. FIG. 2C depicts that the specificity of CD31 aptamer for CD31+ cells was confirmed by flow cytometry. (Q1: Aptamer+CD31−, Q2: Aptamer+CD31+, Q3: Aptamer−CD31+, Q4: Aptamer−CD31−). The aptamer concentration corresponds to the individual graph title. FIG. 2D depicts the specificity and sensitivity of the aptamer for the CD31+ cells. Sensitivity was defined as the fraction of true positive (Aptamer+CD31+/CD31+). The specificity was defined as the fraction of true negatives (Aptamer−CD31−/CD31−) (n=3). FIG. 2E depicts the use of aptamer in magnetic activated cell sorting (MACS) technology for isolating CD31+ cells from PMBCs. Fraction of cell population positively labeled with antibody to CD31 before (Initially) and after enrichment using traditional magnetic beads strategies (MACS positive sorting) and CD31 specific aptamer (Aptamer positive sorting) was shown. Beads were not released from cells prior to analysis. No significant difference was observed in post-enrichment levels of CD31 for antibody and aptamer-mediated processes (n=4, Student's-t-test). No error bar is visible for MACS positive sorting due to really similar high values. Values in FIGS. 2B-2E represent mean and s.d.

Figure 3A:
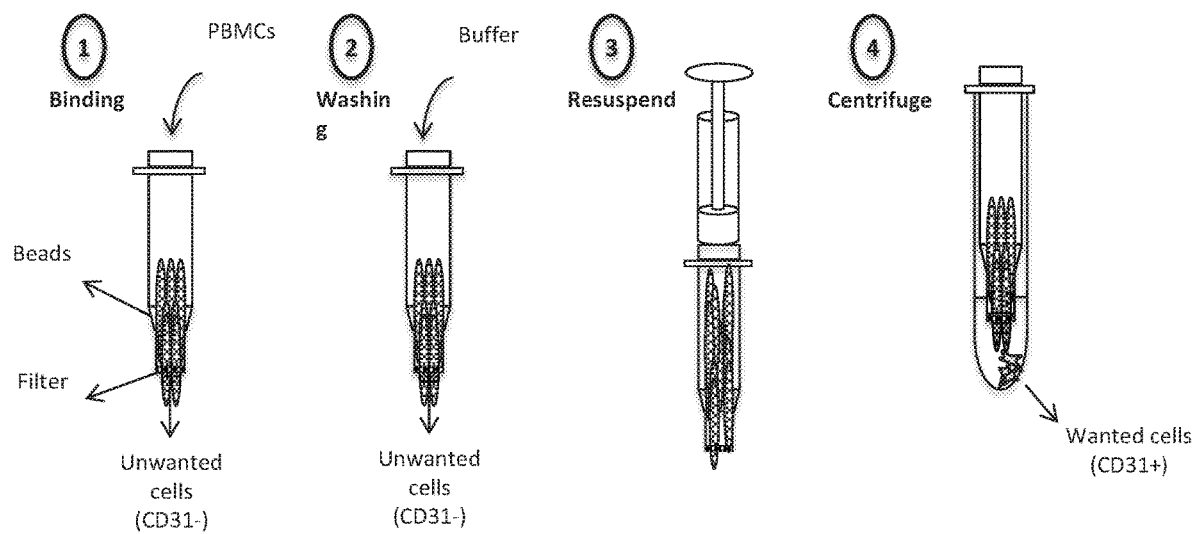
Figure 3B:
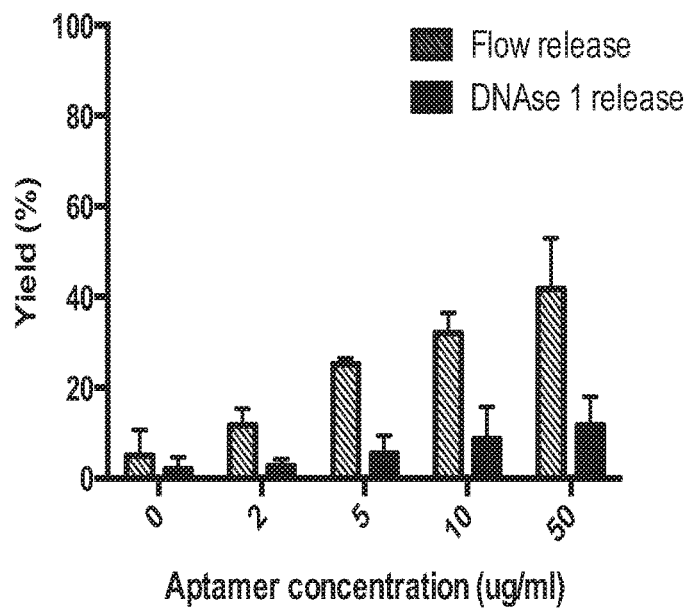
Figure 3C:
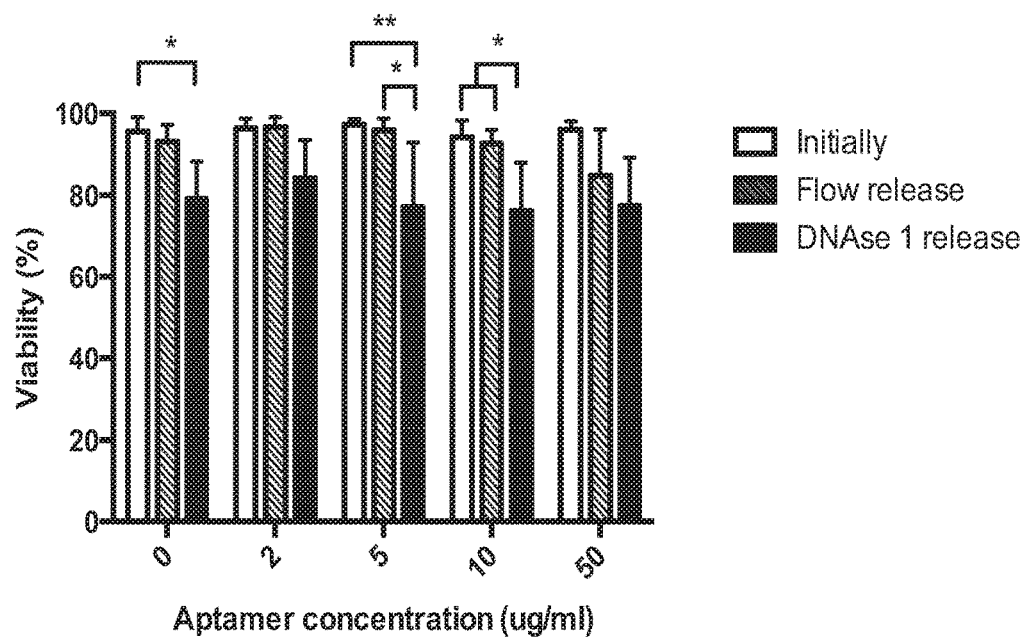
Figure 3D:
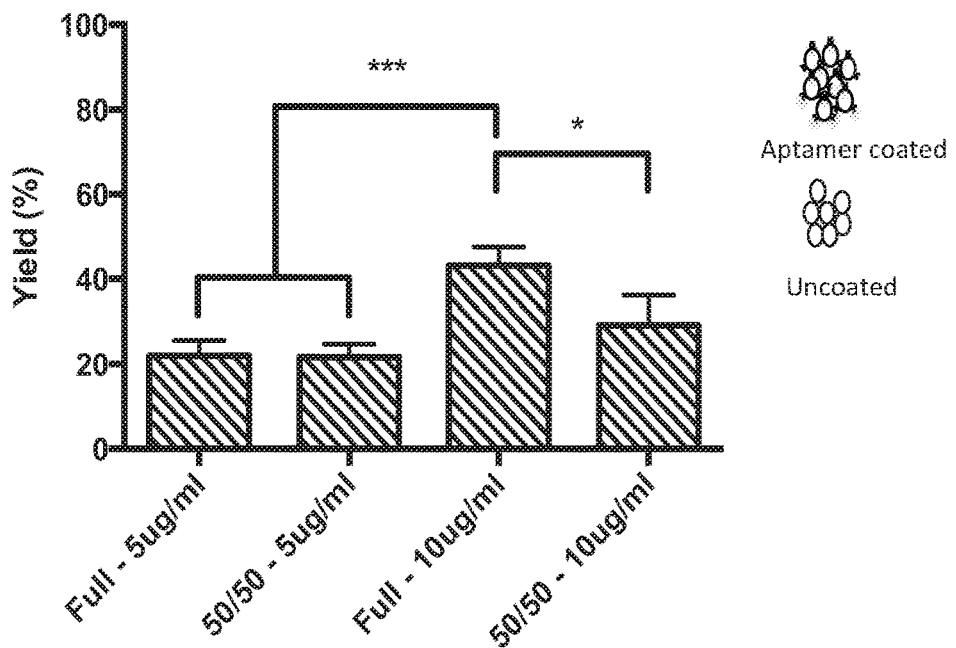

FIGS. 3A-3C depict the concept of CD31+ cell enrichment system and optimization. FIG. 3A depicts the general procedure for the use of aptamer and agarose bead for cell enrichment. (1) Cells were run through the system at low velocity (50 μl/min) to allow binding of CD31+ cells and removal of CD31− cells that pass through the system unimpeded. (2) Any remaining non-adherent cells were removed using PBS buffer wash (300 μl/min). (3) Cells were dissociated from beads by resuspension using a syringe. (4) Tube was centrifuged immediately to collect desired cells (CD31+) that were released from beads. FIG. 3B depicts the effect of aptamer concentration on cell yield and viability. Yield was defined as the number of cells collected after enrichment divided by the number of cells that went through the tube. All the beads were aptamer coated and 800 μl of initial neutravidin agarose bead solution was used per column. DNAse 1 was used at 500 μg/ml for subsequent release (n=3). FIG. 3C depicts the effect of release type and aptamer concentration on cell viability (n=3, data were analyzed using two-way analysis of variance (ANOVA), *=P<0.05, **P<0.01). FIG. 3D depicts the effect of mixing uncoated beads and aptamer coated beads on yield, for two concentrations (5 and 10 μg/ml). Full indicates that all beads were aptamer coated whereas 50/50 indicates that only half of the beads were aptamer coated (n=3, data were analyzed using one-way analysis of variance (ANOVA), *=P<0.05).

Figure 3E:
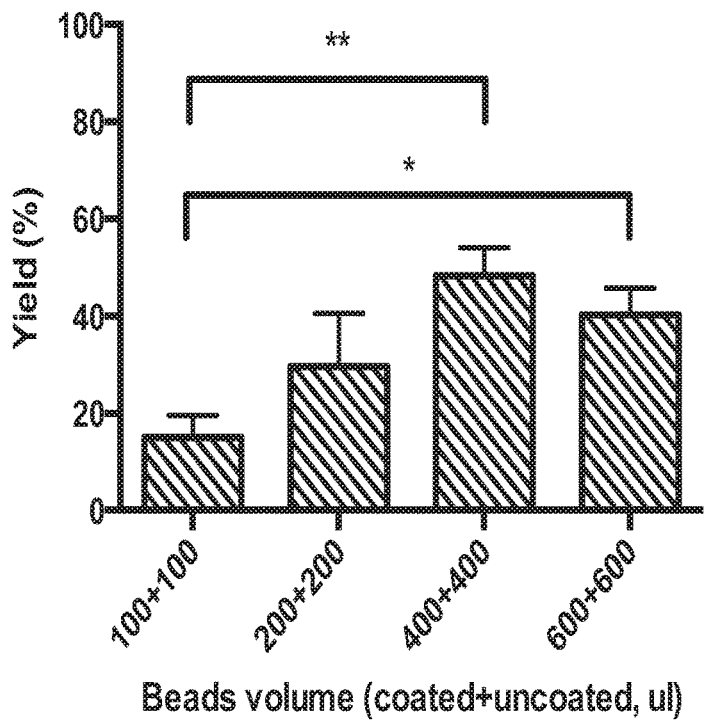

FIG. 3E depicts the yield as a function of initial bead volume suspension. An aptamer concentration of 10 μg/ml was used for aptamer-coated beads. Data are given as A+B where A is the volume of uncoated beads, and B is the volume of coated beads (n=3, data were analyzed using one-way analysis of variance (ANOVA), **P<0.01). Values in FIGS. 3B-3E represent mean and s.d.

Figure 4A:
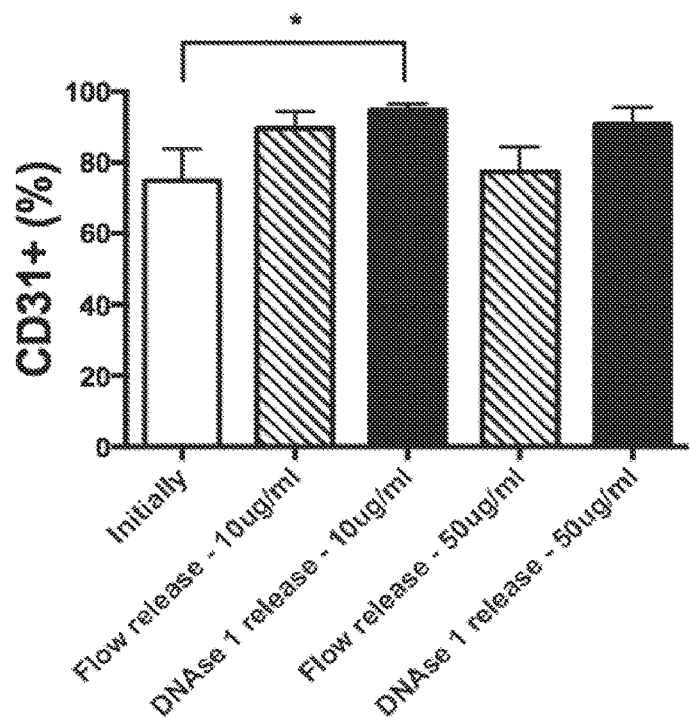
Figure 4B:
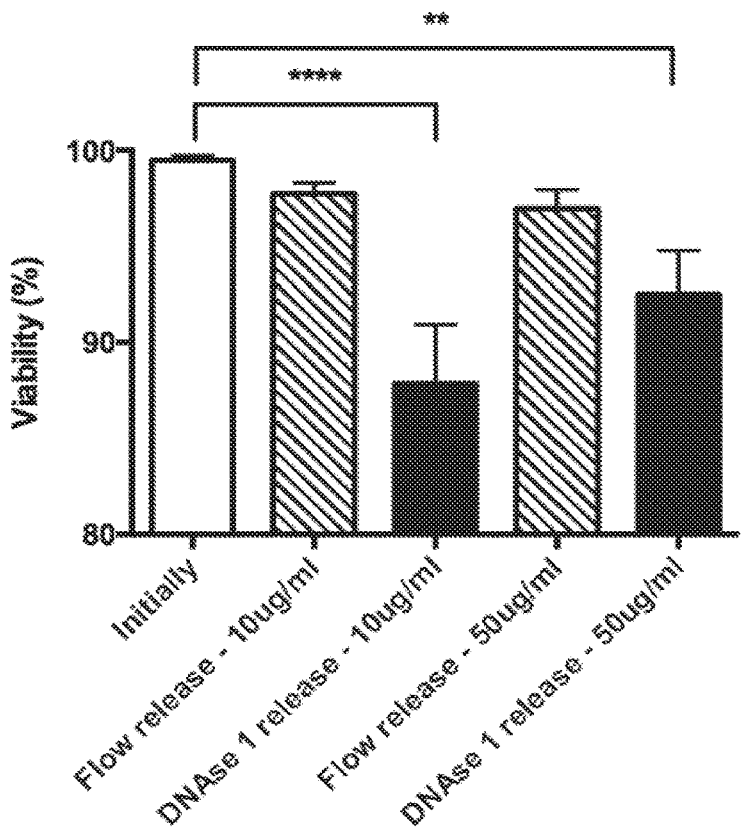

FIGS. 4A-4B depict the effect of DNAse I on cell vitality. FIG. 4A depicts the percentages of cells in the overall PBMCs population that were CD31+, as indicated by antibody staining and FACS analysis, as a function of aptamer concentration and release type (Flow or DNAse 1 release). CD31+ levels were compared before (Initially) and after procedure at two aptamer concentrations (10 and 50 μg/ml) for the two releases (Flow or DNAse 1). FIG. 4B depicts the impact of procedure on cell viability. Cell viability was determined by Muse® Cell Analyzer and evaluated in the initial PBMCs population (Initially) and in the released cell population at two aptamer concentrations (10 and 50 μg/ml) for the two releases (Flow or DNAse 1), n=3. Data were analyzed using one-way analysis of variance (ANOVA). All beads were aptamer coated for this experiment.

Figure 5A:
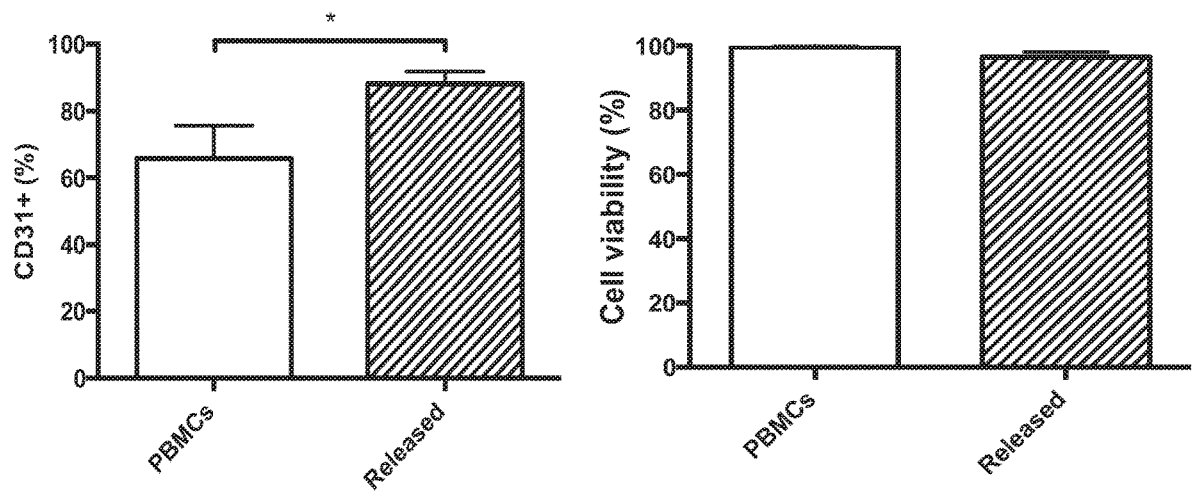
Figure 5B:
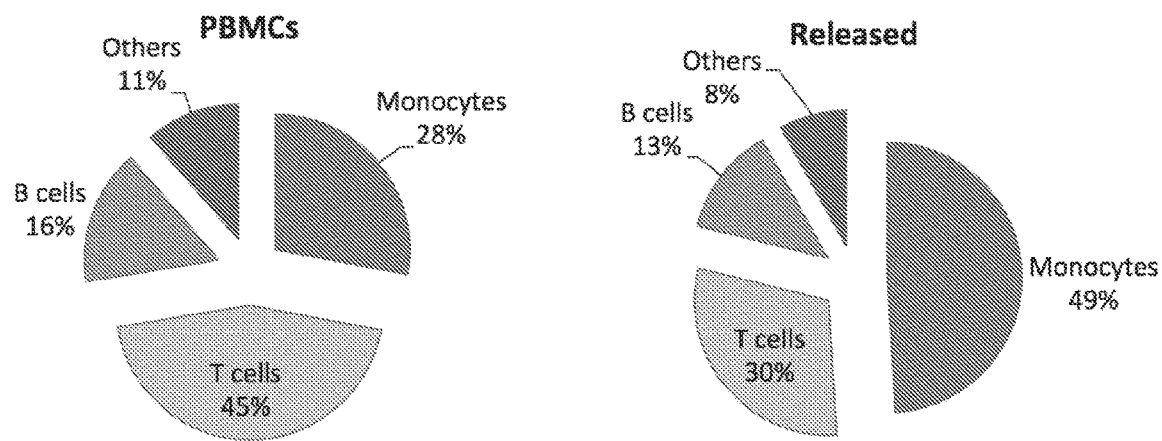

FIGS. 5A-5B depict the enrichment of CD31+ cells from whole blood samples. Specifically, FIG. 5A depicts the percentage of PBMCs that are CD31+, as indicated by antibody staining and FACS analysis, before (PBMCs) and after enrichment using the aptamer-bead column system (Released). The overall increase of CD31+ cells was confirmed without affecting cell viability. FIG. 5B depicts the composition of the CD31+ cell population according to antibody staining and FACS analysis before (PBMCs) and after enrichment (Released) (n=5, values in FIGS. 5A represent mean and s.d., values in FIG. 5B represent mean, data were analyzed using paired Student's t-test, =P<0.01, *P<0.001).

Figure 6A:
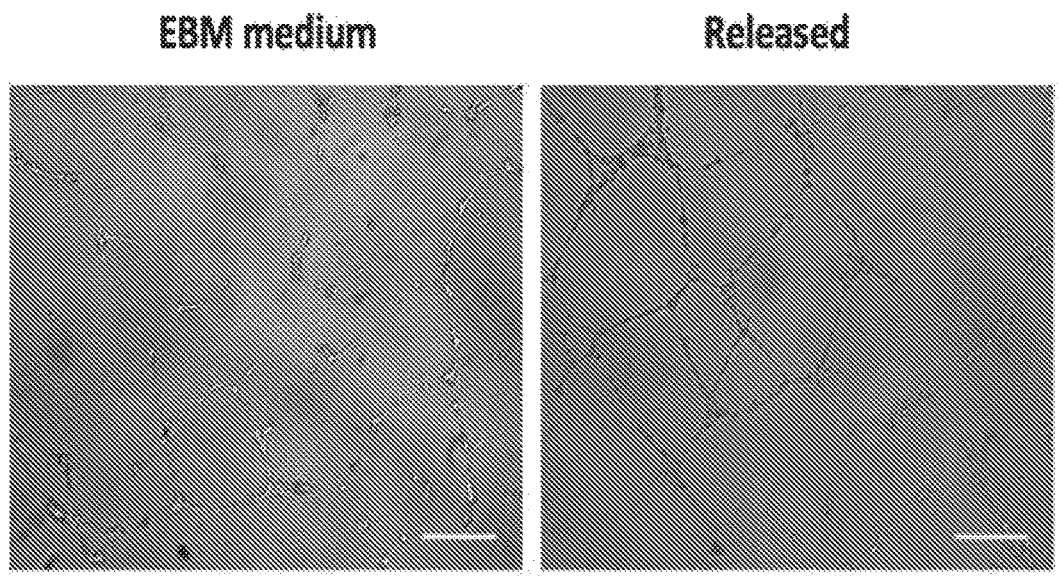
Figure 6B:
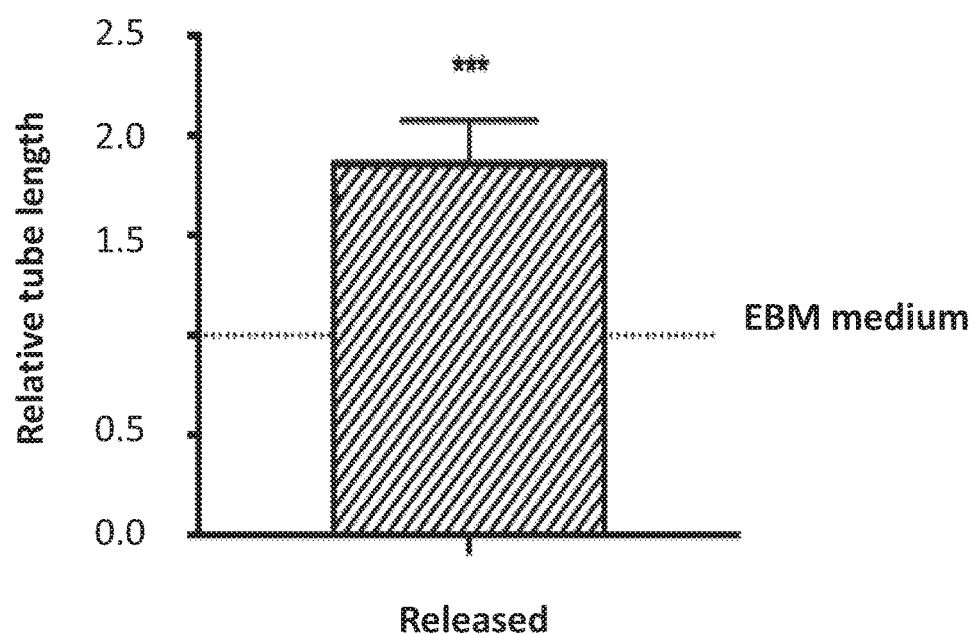
Figure 6C:
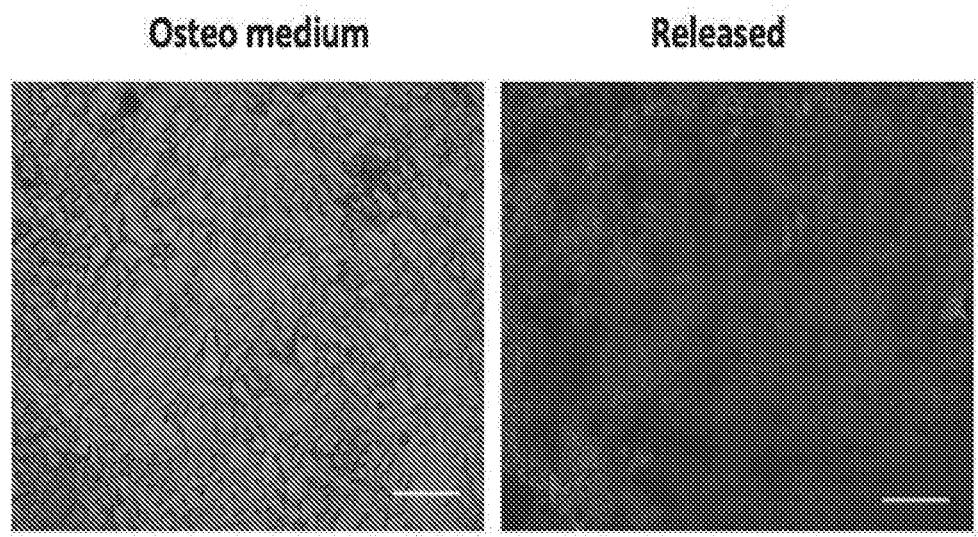
Figure 6D:
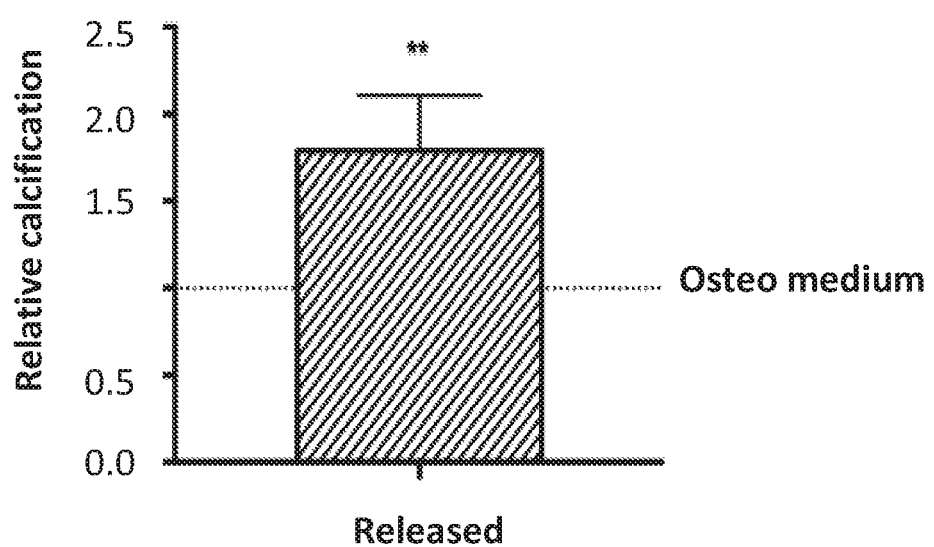

FIGS. 6A-6D depict angiogenic and osteogenic properties of released cell population. FIGS. 6A and 6B depict the angiogenic potential of the enriched CD31+ cells using a tube formation assay. FIG. 6A depicts the microscopic images of HUVECs cultured in endothelial basal medium without addition of angiogenesis activators (EBM medium) or with conditioned medium (50 μl EBM medium +150 μl conditioned medium) from released cell population (Released). FIG. 6B depicts the relative tube length of the enriched CD31+ cells. Relative tube length was calculated and defined as the mean total length of the network for released samples divided by the results obtained for the HUVECS cultured in EBM medium. FIGS. 6C and 6D depict the osteogenic potential of the enriched CD31+ cells by an Alizarin red staining assay. FIG. 6C are images that depict Alizarin red staining of MSCs differentiated for two weeks in osteogenic medium (Osteo medium) or in conditioned medium (½ osteogenic medium+½ conditioned medium, Released). FIG. 6D depicts the relative calcification of enriched CD31+ cells. Relative calcification was calculated and defined as ratio between absorption values obtained by dissolution of matrix-bound ARS using 10% cetylpyridinium divided by values obtained from alamar blue, and normalized to the values obtained for the osteo medium group. (n=5, scale bar=200 um). Values in FIGS. 6B and 6D represent mean and s.d., data were analyzed using paired Student's t-test, *=P<0.05, **P<0.01).

Figure 7:
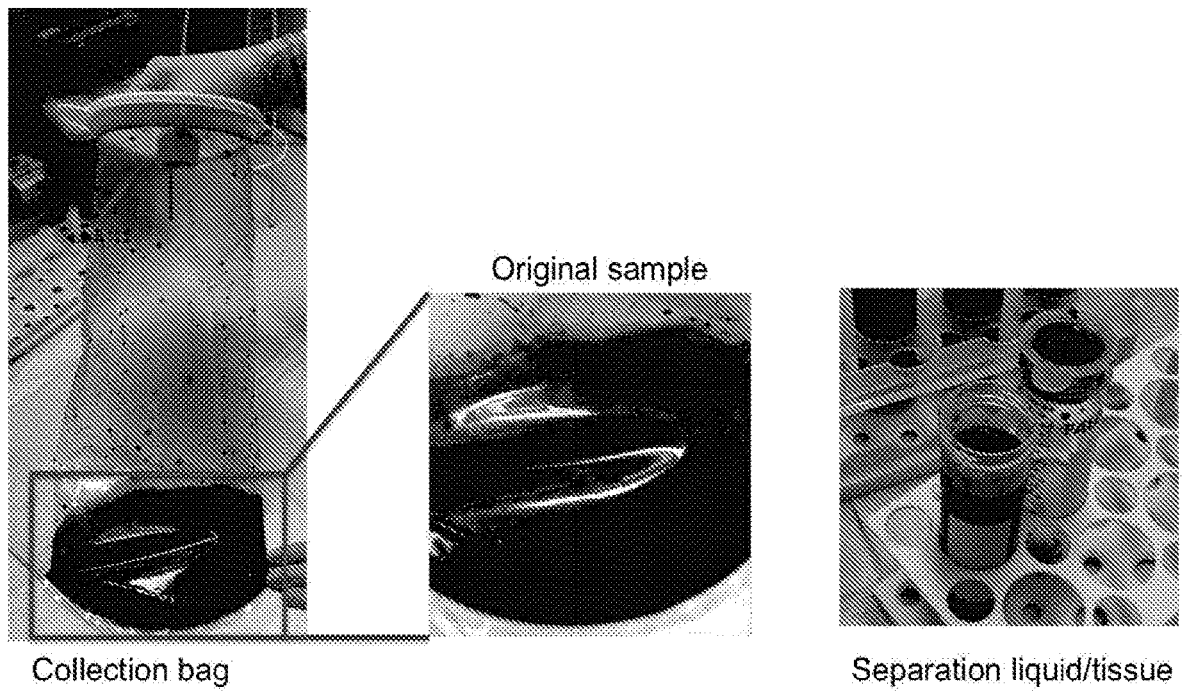

FIG. 7 depicts the collection of suction waste bag postoperatively.

Figure 8:
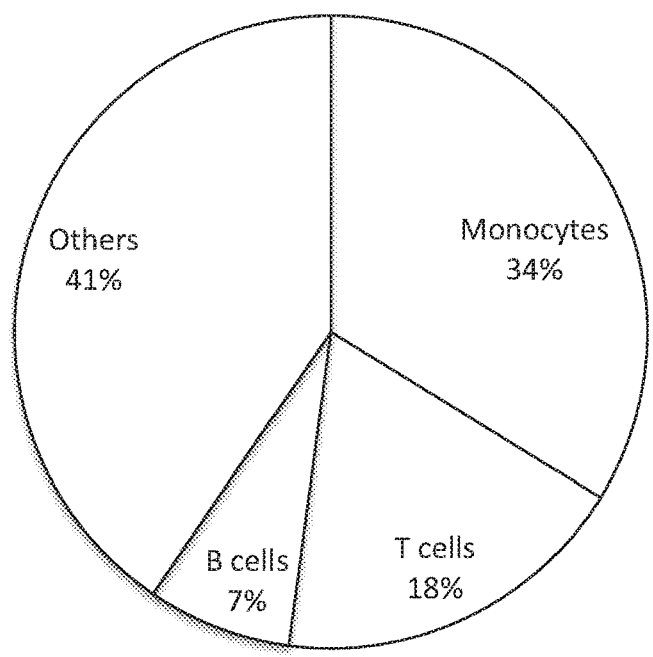
Figure 8:
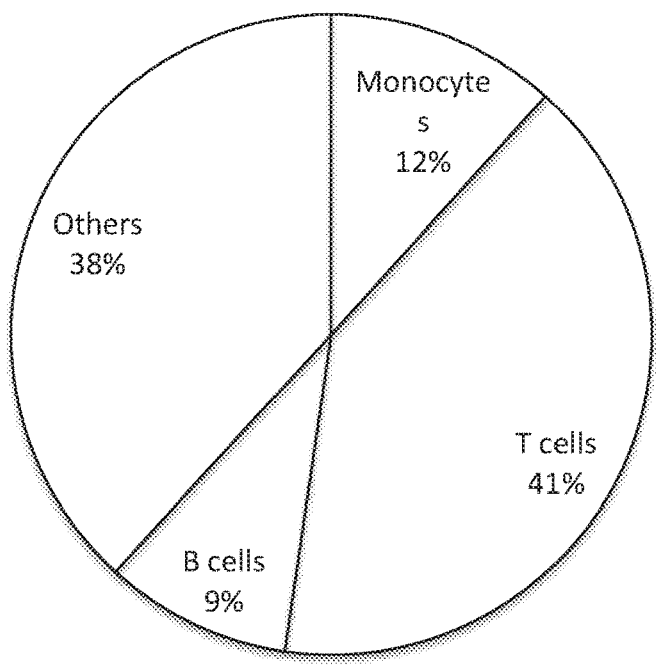

FIG. 8 depicts the composition of the CD31+ fraction within tissue and liquid samples according to antibody staining and FACS analysis (N=3).

Figure 9:
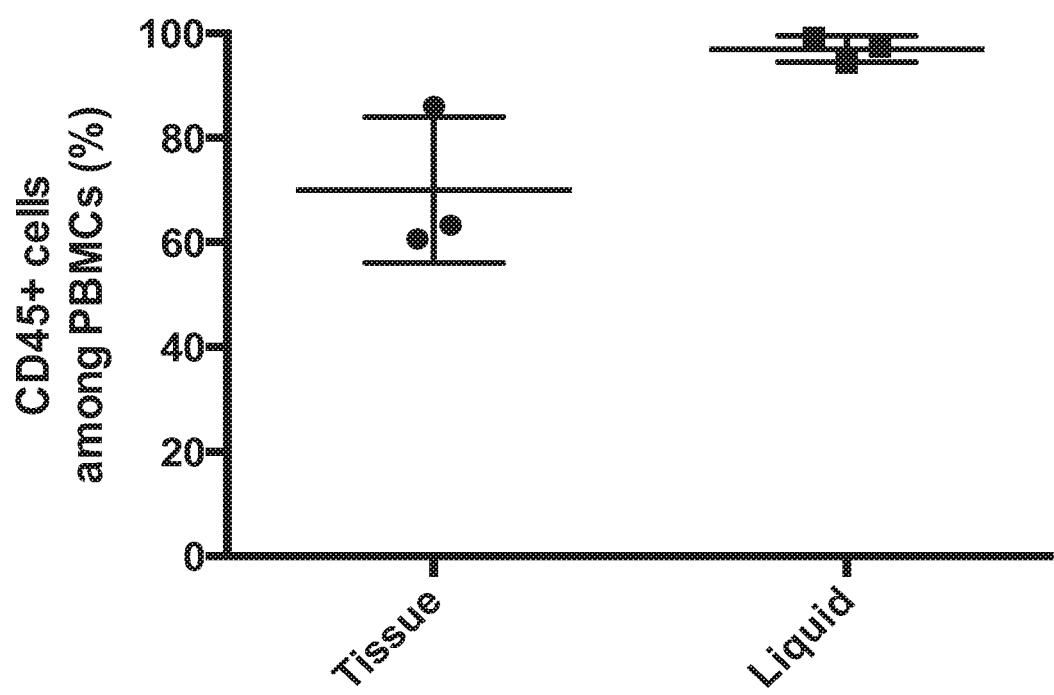

FIG. 9 depicts the levels of CD45+ cells within the tissue and liquid samples according to antibody staining and FACS analysis (N=3).

Figure 10:
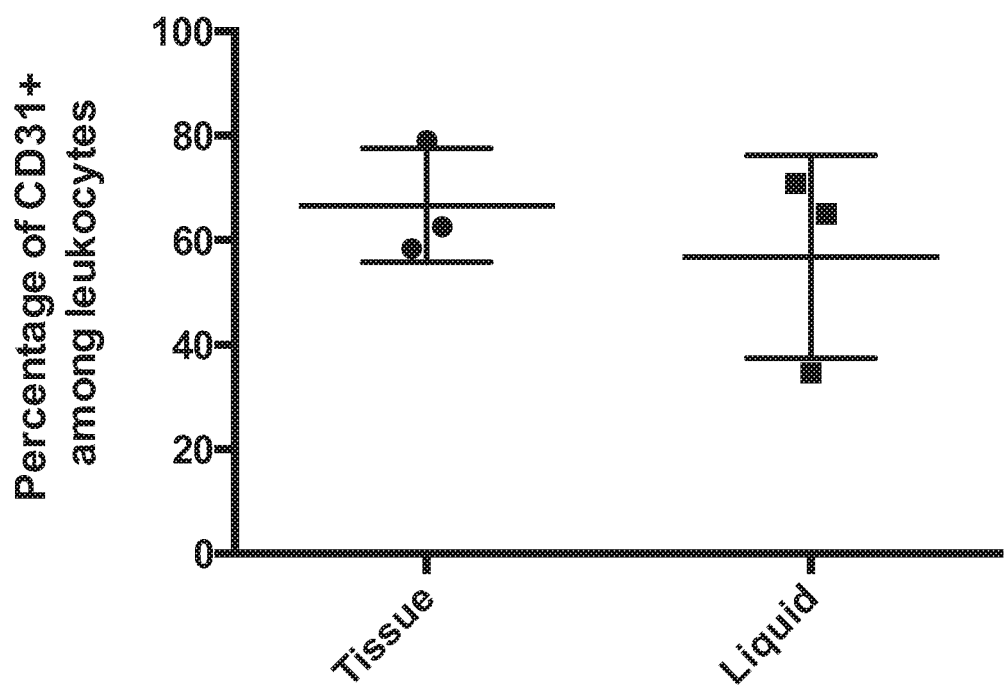

FIG. 10 depicts the initial CD31+ levels among leukocytes within the tissue and liquid samples according to antibody staining and FACS analysis (N=3).

DETAILED DESCRIPTION OF THE INVENTION

The present invention provides devices, methods, and kits for enriching cells with a specific cell surface marker, e.g., CD31+ cells, from a mixed cell population. The invention is based, at least in part, on the discovery that cells bound to an aptamer which specifically recognizes a cell surface protein can be released from the aptamer using mechanical forces, e.g., shear forces, in the absence of any chemical agent to disrupt binding. The device described herein for cell enrichment includes an aptamer suitable for specifically binding the cell surface marker, e.g., CD31. The device can also contain beads having a diameter of about 30-200 µm. The aptamer can be coupled to the beads in a manner that allows for release of selected cells having the cell surface marker, e.g., CD31+ cells, using mechanical forces, in the absence of a chemical agent. The resulting cell population released from the aptamer is enriched for cells containing the cell surface marker, e.g., CD31+ cells, and is substantially free of beads, antibodies, and aptamer. Cells that are enriched or isolated using the device can be used in any application in which an enriched or isolated population of cells is desired.

Due to the rapid nature of cell enrichment using the device, and the lack of beads, antibody, or aptamer on the enriched cells, the device is ideal for intraoperative enrichment of cells obtained from a subject, which are to be administered to a subject during a surgical procedure. Use of the device for intraoperative cell enrichment is illustrated herein using the example of bone healing.

In the US, approximately 7.9 million bone fractures are reported each year with 5 to 10% resulting in an impaired bone-healing situation (Wu et al., *Orthopedic Research and Reviews*. 2013 (5): 21-33; Mills et al., *BMJ open* 2013;3(2). pii: e002276). Predicting patients at risk and initially providing them with additional treatment may significantly reduce the number of non-union cases, and decrease the associated costs and hospital stay (Dahabreh et al., *Injury*. 2007;38: 371-377). Harvesting autologous cells, and intraoperatively enriching them using the device described herein to obtain an appropriate cell population for delivery to the fracture location may improve bone regeneration and bone healing. An exemplary cell population useful for promoting bone healing in a subject is enriched for CD31+ cells.

In order that the present invention may be more readily understood, certain terms are first defined.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "subject," as used herein, refers to either a human or non-human animal. In one embodiment, the subject is a human subject. In another embodiment, the subject is a mammal.

As used herein, the term "isolated" in reference to an isolated cell refers to a cell which is separated from other cells that are present in the natural source of the cell. In one embodiment, an "isolated" cell is substantially free of other cells. A population of cells can also be "isolated" from cells having differing characteristics. For example, cells that express a particular cell surface antigen can be isolated from cells that do not express the cell surface antigen. An isolated population of cells is free or substantially free of cells that do not possess the characteristic of interest. For example, an isolated population of CD31+ cells is free or substantially free of cells that do not express CD31. A cell or population of cells can also be isolated from contaminants, such as reagents used to grow or purify the cell(s), e.g., culture media, beads, antibody, aptamer, etc.

As used herein, the term "enriched" in reference to a population of cells refers to a population of cells in which the proportion of cells possessing a desired characteristic has been increased relative to the proportion of cells possessing the desired characteristic in a starting population of cells. The starting population can include, for example, the natural source material of the cells, e.g., blood. The starting population can also include a population of cells that has previously been processed, sorted, etc. For example, an "enriched" population of CD31+ cells contains a greater proportion of CD31+ cells to CD31− cells than the starting cell population. In embodiments, an enriched population of cells can be enriched for cells possessing a desired characteristic, e.g., antigen expression, by about 5%, 10%, 15%, 20%, 25%, 30%, 40%, 50%, 60%, 70%, 80%, 85%, 90%, 95%, 98%, 99%, or 100%. In other embodiments, an enriched population of cells can be enriched for cells possessing a desired characteristic, e.g., antigen expression, by about 1.5-fold, 2-fold, 3-fold, 4-fold, 5-fold, 10-fold, 15-fold, 20-fold, 30-fold, 40-fold, 50-fold, 60-fold, 70-fold, 80-fold, 90-fold, 100-fold, 250-fold, 500-fold, 1000-fold, 10,000-fold, or more.

The terms "CD31" and "PECAM-1," as used herein, refer to a native CD31 from any vertebrate source, including mammals such as primates (e.g., humans), unless otherwise indicated. The term encompasses full-length, unprocessed CD31, as well as any form of CD31 that results from processing in a cell. The term also encompasses naturally occurring variants of CD31, such as splice variants or allelic variants. The sequence of an exemplary human CD31 nucleic acid sequence is provided herein as SEQ ID NO:1, and the sequence of an exemplary human CD31 amino acid sequence is provided herein as SEQ ID NO:2.

As used herein, the term "aptamer" refers to a nucleic acid molecule, e.g., a single-stranded or a double-stranded nucleic acid molecule, having specific binding affinity for a cell surface marker, e.g., CD31, through interactions other than classic Watson-Crick base pairing. The term encompasses aptamers comprising DNA, RNA, and/or modified oligonucletoides.

As used herein, the term "cell surface marker" or "cell surface antigen" includes antigens that are detectable on the extracellular surface of a cell. Exemplary cell surface markers are proteins, all or a portion of which are localized extracellularly.

The term "substantially free" of a contaminant as used herein means less than 20% of the contaminant, preferably less than 10% of the contaminant, more preferably less than 5% of the contaminant, more preferably less than 2% of the contaminant, and most preferably less than 1% of the contaminant are present.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

I. CD31+ Cells

CD31, as described herein, is also known in the art as Platelet/Endothelial Cell Adhesion Molecule 1 (PECAM-1). CD31 is a cell surface marker that belongs to the immunoglobulin superfamily and is likely involved in leukocyte migration, angiogenesis, and integrin activation. The sequence of an exemplary human CD31 mRNA can be found at, for example, GenBank Accession GI:313760623 (NM_000442.4; provided herein as SEQ ID NO: 1). The sequence of an exemplary human CD31 polypeptide can be found at, for example, GenBank Accession No. GI:313760624 (NP_000433.4; provided herein as SEQ ID NO: 2).

CD31 is found on the surface of platelets, monocytes, neutrophils, and some types of T-cells. CD31 is highly enriched at intercellular junctions of endothelial cells, and plays a role in endothelial cell adhesion and monolayer formation. CD31 can dimerize with itself, and mediates homotypic adhesions in which a CD31 molecule associates in an antiparallel configuration with CD31 on an apposing cell. CD31 additionally binds heparin, as well as integrin $\alpha V\beta 3$.

CD31+ cells are tightly associated with neovascularization, as evidenced by the angiogenic properties, high adhesion capacity and vasculogenic ability of CD31+ cells. In addition, recent studies have shown that CD31+ cells positively impact osteogenesis and have immunomodulator functions that can reduce tissue damage and accelerate tissue regeneration. These functions make CD31+ cells of interest for therapeutic treatment in cardiovascular cell therapy as well as in facilitating bone healing, for example, under impaired healing conditions.

CD31+ cells may be enriched and/or isolated from whole blood, peripheral blood mononuclear cells (PBMCs), or bone marrow. Within the blood, CD31 is expressed on cell types including immune cells such as B cells, T cells, myeloid cells and monocytes. CD31+ cells can also be enriched and/or isolated from blood coming from injured soft tissues within the vicinity of a bone fracture. This material can be obtained, e.g. by suction of injured soft tissues near the fracture site.

Traditional methods for purifying CD31+ cells make use of an immunomagnetic system where magnetic microbeads coupled to anti-CD31+ antibodies are used for selection. The antibodies and/or microbeads can remain attached to cells after positive isolation and potentially get internalized. Other technology involves the use of larger beads which are separated from cells following isolation. Separation of the beads, however, uses a chemical agent in order to release the cells. Other methods, such as fluorescent activated cell sorting, can be utilized to isolate specific cell populations. These methods may be useful for isolating cells for subsequent use in in vitro studies, but are not optimal for therapeutic administration because of the presence of residual antibody or other contaminants that are not compatible for direct administration into human subjects.

The compositions and methods of the present invention allow enrichment and/or isolation of CD31+ cells that are suitable for therapeutic administration, in the absence of contamination from beads, aptamer, antibody, or other undesired agents, e.g., chemical agents. Such methods require minimal manipulation of the CD31+ cell population, relative to current methods of enrichment, e.g., methods which use antibodies to bind cells, and/or methods that rely on chemical agents to release enriched cell populations from a solid support such as beads.

CD31+ cells isolated using the compositions and methods described herein are suitable for administration to a subject without any additional purification or characterization steps. Accordingly, in one embodiment, the invention is particularly suitable for the enrichment of CD31+ cells intraoperatively, as it allows for autologous cells to be rapidly enriched and ready to be administered to a subject in a short period of time, e.g., during the course of a surgical procedure.

II. Aptamers

Aptamers suitable for use in the devices of the invention include single-stranded or double stranded nucleic acid molecules having specific binding affinity for a cell surface marker, e.g., CD31, through interactions other than classic Watson-Crick base pairing. Specifically, aptamers can fold into 3-dimensional structures capable of binding specifically to various biosurfaces, such as cell surface antigens. Aptamers can comprise, for example, DNA, RNA, or modified bases.

Aptamers, like peptides generated by phage display or monoclonal antibodies (MAbs), are capable of specifically binding to selected target molecules. Aptamers created by an in vitro selection process from pools of random sequence oligonucleotides have been generated for over 100 protein targets, including growth factors, transcription factors, enzymes, immunoglobulins, and receptors. An exemplary aptamer suitable for use in the invention is 10-15 kDa in size (about 30-45 nucleotides), specifically binds its target, e.g., a cell surface marker, e.g., CD31, and discriminates against closely related targets (e.g., will typically not bind other proteins from the same gene family).

Aptamers have a number of desirable characteristics for use in cell purification, including high specificity, affinity, and stability. Aptamers also offer specific competitive advantages over antibodies, for example, they can be easily synthesized, and can be chemically manipulated with relative ease. Aptamer synthesis is inexpensive and highly reproducible. For example, aptamers used in the devices of the invention can be produced by solid phase chemical synthesis, an accurate and reproducible process with consistency among production batches. An aptamer can be produced in large quantities by polymerase chain reaction (PCR), and, once the sequence is known, can be assembled from individual naturally occurring nucleotides and/or synthetic nucleotides. Aptamers suitable for use in the devices of the invention are preferably stable during long-term storage at room temperature, and, if denatured, such aptamers can easily be renatured, a feature not shared by antibodies.

Aptamers are particularly suited for use in the devices and methods described herein, because aptamers typically bind their target antigens with high avidity and low affinity. The combined strength of multiple aptamer-antigen interactions is sufficient to capture a cell expressing a cell surface antigen that is bound by an aptamer coupled to a solid support (e.g., a bead). Notwithstanding, as described herein, the strength of individual aptamer-antigen interactions is sufficiently weak that gentle force applied to the cells, e.g., by shaking, pipetting, vortexing, etc., removes the cells from the solid support.

Aptamers selected for use in the devices and methods described herein can, in some embodiments, bind to their target antigen with a Kd of $10^{-3}$ to $10^{-7}$ M. For example, in some embodiments, the aptamer binds a target antigen with a Kd of about $10^{-3}$, $10^{-4}$, $10^{-5}$, $10^{-6}$, $10^{-7}$ M. In other embodiments, the aptamer binds a target antigen with a Kd of about $10^{-4}$ to $10^{-7}$ M. In other embodiments, the aptamer binds a target antigen with a Kd of about $10^{-5}$ to $10^{-7}$ M. In other embodiments, the aptamer binds a target antigen with a Kd of about $10^{-4}$ to $10^{-6}$ M. In other embodiments, the aptamer binds a target antigen with a Kd of about $10^{-6}$ to $10^{-7}$ M. In some embodiments, the aptamer binds a target antigen with a Kd of about $10^{-8}$ M. In some embodiments, the aptamer binds a target antigen with a Kd of about $10^{-9}$ M. In some embodiments, the aptamer binds a target antigen with a Kd of about $10^{-10}$ M.

By way of example, a suitable method for generating an aptamer to a target of interest, e.g., a cell surface marker, such as CD31, for use in the devices of the invention, is with the process known as "Systematic Evolution of Ligands by Exponential Enrichment" ("SELEX™"). The SELEX™ process is a method for in vitro evolution of nucleic acid molecules with highly specific binding to target molecules and is described in, e.g., U.S. Pat. No. 5,475,096 entitled "Nucleic Acid Ligands", and U.S. Pat.. No. 5,270,163 (see also WO 91/19813) entitled "Nucleic Acid Ligands", the entire contents of each of which are incorporated herein by reference.

The SELEX™ methods known in the art may also be used to produce the aptamer suitable for use in the devices of the invention. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes a SELEX™ based methods for selecting nucleic acid ligands containing photoreactive groups capable of binding and/or photocrosslinking to and/or photoinactivating a target molecule. U.S. Pat. No. 5,567,588 and U.S. application Ser. No. 08/792,075, filed Jan. 31, 1997, entitled "Flow Cell SELEX", describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target. The entire contents of each of these patents and applications are incorporated herein by reference.

Counter-SELEX™ is another method that may be used for improving the specificity of an aptamer to a cell surface marker, e.g., CD31. Counter-SELEX™ is comprised of the steps of a) preparing a candidate mixture of nucleic acids; b) contacting the candidate mixture with the target, wherein nucleic acids having an increased affinity to the target relative to the candidate mixture may be partitioned from the remainder of the candidate mixture; c) partitioning the increased affinity nucleic acids from the remainder of the candidate mixture; d) contacting the increased affinity nucleic acids with one or more non-target molecules such that nucleic acid ligands with specific affinity for the non-target molecule(s) are removed; and e) amplifying the nucleic acids with specific affinity to the target molecule to yield a mixture of nucleic acids enriched for nucleic acid sequences with a relatively higher affinity and specificity for binding to the target molecule.

For example, a heterogeneous population of oligonucleotide molecules comprising randomized sequences is generated and selected to identify a nucleic acid molecule having a binding affinity which is selective for a cell surface marker, e.g., CD31 (see, e.g., U.S. Pat. Nos. 5,475,096; 5,476,766; and 5,496,938, the entire contents of each of which are incorporated herein by reference). In some examples, a population of 100% random oligonucleotides is screened. In others, each oligonucleotide in the population comprises a random sequence and at least one fixed sequence at its 5' and/or 3' end. The oligonucleotide can be RNA, DNA, or mixed RNA/DNA, and can include modified or nonnatural nucleotides or nucleotide analogs. (see U.S. Pat. Nos. 5,958,691; 5,660,985; 5,958,691; 5,698,687; 5,817,635; and 5,672,695, PCT publication WO 92/07065, the entire contents of each of which are incorporated herein by reference).

In one embodiment, the aptamer can further comprise a "tag," which refers to a component that provides a means for attaching or immobilizing an aptamer (and any target molecule that is bound to it) to a solid support, such as a bead, e.g., an agarose bead. A "tag" is a set of copies of one type or species of component that is capable of associating with a probe. "Tags" refers to more than one such set of components. The tag can be attached to or included in the aptamer by any method known in the art. Generally, the tag allows the aptamer to associate, either directly or indirectly, with a probe that is attached to the solid support, e.g., a bead. A tag can enable the localization of an aptamer covalent complex to a spatially defined address on a solid support. Different tags, therefore, can enable the localization of different aptamer covalent complexes to different spatially defined addresses on a solid support. A tag can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a probe (or linker molecule, as described below) can be designed or configured to bind or otherwise associate with specificity. Generally, a tag is configured such that it does not interact intramolecularly with either itself or the aptamer to which it is attached or of which it is a part. If SELEX™ is used to identify an aptamer, the tag may be added to the aptamer either pre- or post-SELEX™. In one embodiment, the tag is included on the 5'-end of the aptamer post-SELEX™. In another embodiment, the tag is included on the 3'-end of the aptamer post-SELEX™. In one embodiment, the tag is a biotin molecule. In another embodiment, the tag is a streptavidin molecule.

In another embodiment, an aptamer is attached to a solid support through interactions between the tag and a probe on the beads. A "probe" is a set of copies of one type or species of component that is capable of associating with a tag. "Probes" refers to more than one such set of components. The probe can be attached to or included in the beads by any method known in the art. Generally, the probe allows the bead to associate, either directly or indirectly, with a tag that is attached to the aptamer. A probe can be a polynucleotide, a polypeptide, a peptide nucleic acid, a locked nucleic acid, an oligosaccharide, a polysaccharide, an antibody, an affybody, an antibody mimic, a cell receptor, a ligand, a lipid, any fragment or derivative of these structures, any combination of the foregoing, or any other structure with which a probe can be designed or configured to bind or otherwise associate with specificity with a tag. In one embodiment, the probe is a streptavidin molecule, for example, the streptavidin moiety binds to the biotin groups on the aptamer, thereby localizing the aptamers on the solid support to which the streptavidin-coupled beads are bound. In another embodiment, the probe is a biotin molecule.

Aptamers specific for a cell surface marker of interest, including, anti-CD31 aptamers, are known in the art and are also commercially available. For example, anti-CD31 aptamers are commercially available from Aptamer Sciences, Inc., Gyoungbuk, South Korea ("APTSCI") (CD31 DNA aptamer, product No. CD31-2196BCI/CD31-2196FBCI), and Creative Biogene, Shirley, N.Y., USA (PECAM1/CD31(hu) aptamer, product No. ATP00125).

III. Devices for Enrichment of Cells

In one embodiment, the invention provides devices for enriching a cell population with cells that express a cell surface marker of interest, e.g., CD31. The device contains an aptamer capable of specifically binding the cell surface marker, e.g., CD31, coupled to a solid support. For example, the aptamer can be coupled to beads having a diameter greater than the diameter of the cells to be enriched, wherein the aptamer is coupled to the beads in a manner that allows for release of cells with the cell surface marker, e.g., CD31+ cells, in the absence of a chemical agent. The device optionally comprises a filter containing a pore size smaller than the diameter of the beads, and larger than the diameter of the cells to be enriched. The device can optionally comprise a column containing the beads and the filter. In some embodiments, the column is fitted with a syringe. In some embodiments, the column can be sized to fit in a centrifuge tube. In some embodiments the device further comprises a centrifuge tube housing the column. The device allows production of a cell population enriched for cells expressing a cell surface marker of interest, e.g., CD31, substantially free of beads and aptamer.

The devices of the present invention are suitable for enriching cells with any cell surface marker. In some embodiments, the cell surface marker is expressed on the surface of B cells. In other embodiments, the cell surface marker is expressed on the surface of T cells.

In some embodiments, the cell surface marker is expressed on the surface of monocytes. In other embodiments, the cell surface marker is expressed on the surface of leukocytes. In another embodiment, the cell surface marker is expressed on the surface of a tumor cell.

Exemplary cell surface markers suitable for use in the present invention include, but are not limited to, T-cell receptor (TCR), CD2, CD3, CD5, CD4, CD8, complement receptors, Fc receptors, MHC Class II molecules, membrane immunoglobulin, CD31, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and/or combinations thereof. In some embodiments, the cell surface marker is CD31. Other cell surface markers suitable for use in the invention may include, for example, CD2, CD3, CD4, CD5, CD7, CD8, CD19, CD20, CD21, CD22, CD13, CD14, CD15, CD33, CD16, CD56, CD57, NKB1, CD25, CD26, CD27, CD28, CD38, CD43, CD45RA/RO, CD49A-F, CD69, CD70, CD71, CD80, CD86, CD152, CD154, CD11a, CD11b, CD18, CD29, CD31, CD44, CD54, CD58, CD62, CD102, CD138, CD49a, CD49b, CD49d, CD49e, CD49f, CD51, CD61, CD104; CD105, NGFR; CD15, CD31, CD44, CD50, CD54, CD62E, CD62L, CD62P, CD102, CD106, CD146, CD166, CD10, CD13, CD36, CD55, CD56, CD58, CD59, CD95, HLA-I, HLA-II, β2-microglobuline, TcR, IgM, IgG, IgA, CD16, CD32, CD65, CD25, CD95, CD116M CD120, CD121, CD123, CD124, CD125, CD126, CD127, CD128, CD9, CD35, CD40, CD45, or CD150. Other exemplary cell surface markers include, for example, alfa-fetoprotein (AFP), C-reactive protein (CRP), cancer antigen-50 (CA-50), cancer antigen-125 (CA-125) associated with ovarian cancer, cancer antigen 15-3 (CAI5-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdrl gene product), multidrug-resistance-related antigen, p 170, multidrug-resistance-related antigen, prostate specific antigen (PSA), CD56, NCAM; hemoglobin A, glycophorin A, gpIIbIIIa, the erythropoietin receptor, CD3, CD9, CD10, CD13, CD14, CD19, CD34, CD38, CD45, CD90, CD133, CD11b, CD33, CD36, CD41, MO1, OKT3, OKT4, OKT8, OKT11, OKT16, OKM1, OKMS, Leu7, Leu, Leu M1, Leu M3, acetylcholinesterase, glial fibrillary acidic protein (GFAP) and myelin basic protein, human milk fat globule antigen (HMFG), keratins, or crystallins.

The foregoing cell surface markers are provided as an illustration of the vast number of cell surface markers that may be used in the devices of the present invention, and is not intended to be limiting.

In some embodiments, the beads are packed in a column. In other embodiments, the beads are present in a suspension and collected by centrifugation. The column containing the beads can be of a size and character to allow release of cells without removal of beads. In some embodiments, the column can be of a volume of about 1 mL, 2 mL, 3 mL, 4 mL, 5 mL, 6 mL, 7 mL, 8 mL, 9 mL, 10 mL, 15 mL, 20 mL, 30 mL, 40 mL, 50 mL, 60 mL, 70 mL, 80 mL, 90 mL, 100 mL, 500 mL, 1000 mL, etc. To facilitate removal of cells from beads, the column can be sized to fit in a centrifuge tube, for example, a small eppendorf tube or a large falcon tube, such that cells can be collected by centrifugation using either a tabletop centrifuge or a large centrifuge. When beads are packed in a column, the column can contain a filter with pores sized to allow cells to pass through while retaining beads in the column. In one embodiment, the filter has a pore size smaller than the diameter of the beads. In another embodiment, the filter has a pore size larger than the diameter of the cells to be enriched. In a some embodiments, the filter has a pore size of, for example, about 10-100 µm, e.g., about 10 µm, 20 µm, 30 µm, 40 µm, 50 µm, 60 µm, 70 µm, 80 µm, 90 µm, or 100 µm. In other embodiments, the filter has a pore size of about 10-50 µm, about 10-30 µm, about 10-25 µm, about 10-20 µm, or about 10-15 µm. In some embodiments, the filter has a pore size of less than 10 µm.

The size of beads that are used in the device can vary. In some embodiments, the bead is larger than a cell. In other embodiments, the beads are larger than the pore size of the filter. In some embodiments, the beads have a diameter of about 30-200 µm. In some embodiments, the beads have a diameter of about 30-150 µm. In other embodiments, the beads have a diameter of about 50-150 µm. In some embodiments, the beads have a diameter of about 20 µm, 30 µm, 40 µm, 50 µm, 60 µm, 70 µm, 80 µm, 90 µm, 100 µm, 110 µm, 120 µm, 130 µm, 140 µm, 150 µm, 160 µm, 170 µm, 180 µm, 190 µm, or 200 µm. In some embodiments, the beads have a diameter greater than 200 µm. In further embodiments, the beads are packed in a column. When beads are packed in a column containing a filter, it can be advantageous to use beads having a diameter larger than the diameter of the pores in the filter, so that the beads will not pass through the filter, and will be retained in the column.

The beads used in the devices and methods described herein can comprise any standard material known in the art to suitable for cell-based chromatography, for example, agarose beads, sepharose beads, polystyrene beads, etc. In exemplary embodiments, the beads are not magnetic.

Regulatory agencies have expressed concerns regarding the suitability of cells enriched using magnetic beads substantially smaller than the cell diameter (e.g. beads having a diameter in the nanometer to micrometer range) for clinical use. Concerns include the possibility of beads contaminating the final product, or phagocytosis of the beads by the cells. The devices described herein overcome such concerns by preferably using beads larger than the diameter of the cells to be enriched, eliminating the possibility that the beads will be phagocytosed, and preferably using a filter having a pore size smaller than the diameter of the beads and larger than the diameter of the cells to be enriched, allowing beads and cells to be easily separated.

Beads can be easily separated from the captured cells of interest by applying mechanical forces, without the addition of any other reagents. As a result, the isolated cell population is free or substantially free of beads, aptamer, antibody, or any other undesired reagents. In some embodiments, mechanical forces can be applied to the beads without removing them from the column. Release of captured cells, e.g., CD31+ cells, can be accomplished by, for example, resuspension in a buffer, shaking, pipetting, or vortexing the aptamer-coupled beads. In other embodiments, the column is fitted with a syringe. The syringe can be used to mechanically agitate the beads/cells, thereby disrupting the interaction between beads and cells. The use of mechanical force to separate cells from the aptamer coated beads allows the bound cells to be released without adding any extraneous reagents that could subsequently contaminate the cell population and limit the use of the cell population in clinical applications.

In other embodiments, captured cells can be released from the device using a change in temperature. For example, the beads can be exposed to a temperature sufficient to denature the aptamer. In the case of a nucleic acid-based aptamer, cells can be released by exposure to temperatures of about 95° C. or greater for a period of time sufficient to denature nucleic acid, e.g., about 1 minute, about 2 minutes, about 3 minutes, about 4 minutes, about 5 minutes, etc. In some embodiments the period of time is about 5-10 minutes. In other embodiments, the period of time is about 20 minutes. In other embodiments, the period of time is 30 minutes or less. In applications where it is desirable to obtain an enriched population of viable cells with a cell surface marker, e.g., CD31+ cells, the cells are exposed to elevated temperatures for a minimal amount of time sufficient to denature the nucleic acid aptamer and release the cells, without significantly impacting cell viability.

In other embodiments, captured cells can be released from the device using a nucleic acid molecule complementary to all or a part of the nucleic acid aptamer. Complementary nucleic acid molecules can compete for binding to the aptamer with cells containing the antigen, causing release of cells when the aptamer binds to the complementary nucleic acid.

Temperature and/or complementary nucleic acid can be used to release cells from the aptamer independently or in conjunction with mechanical disruption, as described herein.

The aptamer can be coupled to the solid support, e.g., beads, in a manner suitable for release of cells expressing the antigen bound by the aptamer, e.g., CD31+ cells, in the absence of a chemical agent, to thereby produce a cell population enriched for cells expressing the antigen substantially free of beads and aptamer. Interaction between aptamer and beads should be sufficiently strong to allow release of the cells using mechanical force without removing the aptamer from the beads. Such an interaction can be accomplished by non-covalently coupling the aptamer to the beads. For example, the aptamer can be non-covalently coupled to the beads through interaction of streptavidin and biotin. In one embodiment, the aptamer is biotinylated, the beads are coupled to streptavidin, and the aptamer is coupled to the beads through the interaction of biotin and streptavidin. Alternatively, in another embodiment, the aptamer is coupled to streptavidin, and the beads are biotinylated. A person skilled in the art will recognize that other moieties can be substituted for streptavidin and retain the binding capacity for biotinylated ligand, e.g., avidin, NeutrAvidin, etc. In some embodiments, interaction between aptamer and beads can be accomplished by covalently coupling the aptamer to the beads. In some embodiments, the aptamer is present at a concentration of about 1-50 µg aptamer/mL beads, e.g., 10-40 µg/mL, 20-50 µg/mL, 30-50 µg/mL, 5-10 µg/mL, 5-25 µg/mL, or 10-20 µg/mL. In one embodiment, the aptamer is present at a concentration of 10 µg/mL. Aptamer may be loaded on beads using any art-recognized method. For example, the anti-CD31 aptamer may be attached to the beads by suspending the beads in a aptamer containing solution followed by a 20 minute incubation at 4° C. The aptamer coupled beads can be subsequently collected by centrifugation.

After release from the beads, selected cells, e.g., CD31+ cells, can be recovered from the beads, using any suitable method. In embodiments in which the device contains a column fitted with a filter having pores of a diameter intermediate to that of the cells and the beads, released cells can be recovered by separation through the filter. Upon passing through the filter, cells can be collected and recovered, e.g., by centrifugation. The recovered cell fraction is enriched for cells that express the cell surface marker bound by the aptamer. In some embodiments, the recovered cell fraction is substantially free of cells that do not express the cell surface marker bound by the aptamer. In such embodiments, the recovered cell fraction expressing the cell surface marker of interest has been isolated from cells that do not express the cell surface marker. Cells enriched, purified, or isolated using the devices described herein are advantageously free or substantially free of beads, aptamer, antibody, nuclease, or any additional agents that are added to facilitate the release of cells, avoiding the possibility of a potential contaminant remaining in the final cell suspension.

In some embodiments it can be advantageous to use a mixture of beads coupled to the aptamer and beads not coupled to the aptamer. The presence of a large quantity of aptamer coupled beads may spatially block the interaction between cells and the beads. As such, mixing aptamer-free beads with aptamer-coupled beads may reduce, to some extent, the steric hindrance while maintaining sites for interaction between the aptamer and cells expressing the cell surface marker of interest, e.g., CD31+ cells. The ratio of aptamer-coupled beads to aptamer-free beads in the devices of the invention include, but are not limited to, 1:1, 2:1, 3:1, 4:1, 5:1, 10:1, or 20:1. In exemplary embodiments, the ratio of aptamer-coupled beads to aptamer-free beads is 1:1, 2:1 or 3:1. In other embodiments, the ratio of aptamer-coupled beads to aptamer-free beads in the devices of the invention include, for example, 1:2, 1:3, 1:4, 1:5, 1:10 or 1:20.

In an exemplary embodiment, the device contains beads coupled to an aptamer that binds CD31. Such a device can be used to enrich and/or isolate CD31+ cells from a mixed cell population (e.g., whole blood, peripheral blood, suction blood from a wound site, etc.).

In some embodiments, the device is portable. A portable device is capable of being transported and can, for example, be easily carried or conveyed by hand. A portable device for cell purification, isolation or enrichment is advantageous as the device can be transported easily such that the procedure can be performed at any location where the device can be fitted. For example, the portable device can be used during the course of a surgical procedure and be carried from one surgical room to another. In some embodiments, the device is a closed system.

In some embodiments, the device is prepackaged in a sterile container. A sterile container is free from living germs or microorganisms, e.g., an aseptic container. As such, cells isolated using the device can be administered directly to a subject, for example, to the subject by introduction at a surgical site. Enriched cell populations can be administered at the site of any type of injury. For example, cell populations enriched for CD31+ cells can be administered to the subject at the site where osteogenesis and/or angiogenesis is desired, e.g., the site of a bone fracture, or a site of non-union. In some embodiments, the cell populations enriched for cells with a cell surface marker, e.g., CD31+ cells, are administered by injection.

Although the invention is described herein with respect to devices which comprise aptamers coupled to beads which are suitable for enriching cells with a cell surface marker, e.g., CD31+ cells, the present invention may, in some embodiments, include devices which comprise any antigen binding moiety, e.g., antibody, or antigen-binding portion thereof, (e.g., an antibody or antigen-binding portion thereof that weakly binds antigen), integrin, DNA, RNA, small molecule, natural ligand, etc. coupled to a bead for enriching live cells from a mixed cell population. Thus, for example, in some embodiments, the present invention provides a device for enriching live cells from a broader population based on one or more desirable surface antigens which comprises one or more ligands which interact with the target antigen(s) in a relatively weak/reversible manner (e.g., with a Kd of $10^{-3}$ to $10^{-7}$ M, e.g., a Kd of about $10^{-3}$, $10^{-4}$, $10^{-5}$, $10^{-6}$, $10^{-7}$ M); and beads having a diameter of about 30-200 μm; wherein the ligand or ligands are coupled to beads and collectively adhere to target cells via a multitude of weak/reversible interactions. The cells may be released from the ligands and beads by disrupting their collective interactions with or without additional chemical agents, producing a cell sub-population enriched for the antigens of interest but substantially free of beads and ligands.

The devices described herein are exemplified using aptamer-coupled beads. Other solid supports can, in some embodiments, be used in place of beads for performing cell enrichment. For example, in some embodiments, the device can contain microfluidic or tube-based solid support coupled to the aptamer.

IV. Methods of Enriching Cells from a Mixed Cell Population

The present invention also provides methods for enriching cells that express a cell surface marker of interest from a mixed cell population, i.e., population of cells that contains cells expressing the antigen of interest, and cells that do not express the antigen of interest. The method involves providing aptamer-coupled beads, wherein the aptamer specifically binds a cell surface marker of interest; contacting the aptamer-coupled beads with a mixed cell population; washing the aptamer-coupled beads with a wash buffer such that unbound cells (i.e., cells without the cell surface marker), are removed from the cell sample; subjecting the aptamer-coupled beads to a mechanical force sufficient to release bound cells (i.e., cells expressing the cell surface marker) from the aptamer-coupled beads; and recovering the cells expressing the cell surface marker, from the aptamer-coupled beads. In this manner, a cell population that is enriched in cells expressing a cell surface marker is produced. Preferably, the enriched cell population is free or substantially free of beads and/or aptamer. In some embodiments, the enriched cell population is substantially free of cells that do not express the cell surface marker of interest. In such embodiments, the method produces an isolated cell population of cells expressing the antigen of interest.

The aptamer-coupled beads can be contacted with the mixed cell population for a period of time sufficient for the aptamer to specifically bind the antigen of interest expressed on the surface of a subpopulation of the cells. In embodiments, the aptamer-coupled beads are allowed to remain in contact with the mixed cell population for a period of about 1-30 minutes or more, e.g., at least about 1 minute, at least 2 minutes, at least 3 minutes, at least 4 minutes, at least 5 minutes, at least 6 minutes, at least 7 minutes, at least 8 minutes, at least 9 minutes, at least 10 minutes, at least 12 minutes, at least 15 minutes, at least 20 minutes, at least 25 minutes, at least 30 minutes or more. In one embodiment, the aptamer-coupled beads are allowed to remain in contact with the mixed cell population for 30 minutes or more. In one embodiment, the aptamer-coupled beads are allowed to remain in contact with the mixed cell population for a period of about 45 minutes. In one embodiment, the aptamer-coupled beads are allowed to remain in contact with the mixed cell population for a period of about 60 minutes. In another embodiment, the aptamer-coupled beads are allowed to remain in contact with the mixed cell population for less than one minute. Preferably, the aptamer-coupled beads are contacted with the mixed cell population for the minimal time within which the aptamer can specifically bind the antigen of interest. The time of incubation sufficient for the aptamer to specifically bind the antigen of interest may be related to some extent to the temperature at which the binding occurs. In exemplary embodiments, binding of cells expressing an antigen of interest to an aptamer occurs at 4° C.-37° C. In one embodiment, binding occurs at about 4° C.

In another embodiment, binding occurs at room temperature (e.g., about 21° C.-23° C.). In one embodiment, binding occurs at about 4° -23° C.

The methods of the present invention are suitable for enriching cells with any cell surface marker of interest. In some embodiments, the cell surface marker is expressed on the surface of B cells. In other embodiments, the cell surface marker is expressed on the surface of T cells. In some embodiments, the cell surface marker is expressed on the surface of monocytes. In other embodiments, the cell surface marker is expressed on the surface of leukocytes. In another embodiment, the cell surface marker is expressed on the surface of a tumor cell. Exemplary cell surface markers suitable for use in the present invention include, but are not limited to, T-cell receptor (TCR), CD2, CD3, CD5, CD4, CD8, complement receptors, Fc receptors, MHC Class II molecules, membrane immunoglobulin, CD31, CD11, CD14, CD16, CD19, CD24, CD28, CD29, CD34, CD43, CD44, CD45, CD49, CD53, CD57, CD68, CD84, CD90, CD97, CD117, CD133, CD155, CD166, CD200, CD244, CD300, CCR1, CCR2, CCR3, CCR5, CCR6, CCR8, CXCR1, CXCR4, CXCR6, CX3CR1, ESA, P63, stem cell antigen, NCAM, Thy-1, c-Kit, Flt-3, and/or combinations thereof. In some embodiments, the cell surface marker is CD31.

Captured cells expressing the cell surface marker, e.g., CD31+ cells, can be released from the aptamer-coupled beads using mechanical forces, as described herein. In some embodiments, mechanical forces can be applied to the beads without removing them from the column. Release of cells with a cell surface marker, e.g., CD31+ cells, can be accomplished by, for example, resuspension in a buffer, shaking, pipetting, or vortexing the aptamer-coupled beads. In some embodiments, the mechanical force is applied by resuspension of the aptamer-coupled beads in a resuspension buffer, wherein the resuspension buffer does not contain an agent capable of releasing the cells with a cell surface marker, e.g., CD31+ cells, from the aptamer-coupled beads. Agents capable of releasing cells from beads during cell-based chromatography are known in the art. In one embodiment, the agent is a nuclease. In another embodiment, the agent is a protease. In another embodiment, the agent is DNase. In an alternative embodiment, the agent is RNase. In one embodiment, the agent is a complementary strand of an aptamer. Accordingly, in embodiments, the cells are released from the beads in the absence of agents including nucleases, proteases, DNases, RNases, and/or nucleic acid complementary to the aptamer, and combinations thereof. The resuspension buffer can be any water-based salt solution known in the art that has an osmolarity and ion concentration that are suitable for use with cells of the human body. In one embodiment, the resuspension buffer is phosphate buffered saline (PBS).

In other embodiments, captured cells with a cell surface marker, e.g., CD31+ cells, can be released from the device using a change in temperature. For example, the beads can be exposed to a temperature sufficient to denature the aptamer. In the case of a nucleic acid-based aptamer, cells can be released by exposure to temperatures of about 95° C. or greater for a period of time sufficient to denature nucleic acid, e.g., about 1 minute, about 2 minutes, about 3 minutes, about 4 minutes, about 5 minutes, etc. In some embodiments the period of time is about 5-10 minutes. In other embodiments, the period of time is about 20 minutes. In other embodiments, the period of time is 30 minutes or less. In applications where it is desirable to obtain an enriched population of viable cells with a cell surface marker, e.g., CD31+ cells, the cells are exposed to elevated temperatures for a minimal amount of time sufficient to denature the nucleic acid aptamer and release the cells.

In other embodiments, captured cells with a cell surface marker, e.g., CD31+ cells, can be released from the device using a nucleic acid molecule complementary to all or a part of the nucleic acid aptamer. Complementary nucleic acid molecules can compete with cells with a cell surface marker, e.g., CD31+ cells, for binding to the aptamer, causing release of cells when the aptamer binds to the complementary nucleic acid.

Temperature and/or complementary nucleic acid can be used to release cells from the aptamer independently or in conjunction with mechanical disruption, as described herein. The foregoing method can be performed using any embodiment of the device described herein. For example, the beads can be packed in a column, or present in a suspension. In some embodiments, the column containing the beads can be of a size and nature to allow release of cells without removal of beads. The column can be of a volume of about 1 mL, 2 mL, 3 mL, 4 mL, 5 mL, 6 mL, 7 mL, 8 mL, 9 mL, 10 mL, 15 mL, 20 mL, 30 mL, 40 mL, 50 mL, 60 mL, 70 mL, 80 mL, 90 mL or 100 mL. To facilitate removal of cells from beads, the column can be sized to fit in a centrifuge tube, for example, a small eppendorf tube or a large falcon tube, such that the beads can be collected by centrifugation using either a tabletop centrifuge or a large centrifuge. When beads are packed in a column, the column can contain a filter with pores to allow cells to pass through while retaining beads in a column. In one embodiment, the filter has a pore size smaller than the diameter of the beads. In another embodiment, the filter has a pore size larger than the cells to be enriched. In an exemplary embodiment, the filter has a pore size of, for example, less than 30 μm, less than 25 μm, less than 20 μm, less than 15 μm, or less than 10 μm. In other embodiments, the column is fitted with a syringe. The syringe can be used to mechanically disrupt the interaction between beads and cells in the absence of any additional reagents, and to control the flow rate during the cell enrichment procedure.

In embodiments where the aptamer-coupled beads are provided in a column, the method can further comprise a step of passing the mixed cell population through the column. The flow rate of the column can be controlled to allow the cells to contact the aptamer-coupled beads for a period of time sufficient for cells expressing the antigen of interest to bind the aptamer. A fast flow rate will not provide enough time for cells to interact with aptamer-coupled beads. Alternatively, non-specific binding between the aptamer and cells without the specific cell surface marker, e.g., CD31− cells, may occur as a result of a slow flow rate. In exemplary embodiments, the cells are run through the column at a flow rate of about 5-100 μL/min. In another exemplary embodiment, the cells are run through the column at a flow rate of about 50 μL/min. In another exemplary embodiment, the cells are run through the column at a flow rate of 100 μL/min, 95 μL/min, 90 μL/min, 85 μL/min, 80 μL/min, 75 μL/min, 70 μL/min, 65 μL/min, 60 μL/min, 55 μL/min, 50 μL/min, 45 μL/min, 40 μL/min, 35 μL/min, 30 μL/min, 25 μL/min, 20 μL/min, 15 μL/min, 10 μL/min or 5 μL/min.

Beads used in methods described herein may have various sizes. In some embodiments, the beads are larger than a cell. In other embodiments, the beads are larger than the pore size of the filter. In some embodiments, the beads have a diameter of about 30-200 μm. In other embodiments, the beads have a diameter of about 50-150 μm, or a diameter of about 100-150 µm. For example, the beads have a diameter of about 50 µm, 60 µm, 70 µm, 80 µm, 90 µm, 100 µm, 110 µm, 120 µm, 130 µm, 140 µm or 150 µm.

The composition of the beads can also vary. Any standard beads known in the art for cell-based chromatography can be used in the method described herein, for example, agarose beads. Alternatively, the beads are sepharose beads. Another example of the beads is a polystyrene bead, for example, polystyrene beads from the company Spherotech. In an exemplary embodiment, the beads are not magnetic. The use of larger and non-magnetic beads for enriching cells with a cell surface marker, e.g., CD31+ populations, as described herein is highly advantageous when compared to existing technologies, as cells with a cell surface marker, e.g., CD31+ cells, isolated using the compositions and methods described herein are free or substantially free of beads, aptamer, antibody, or any other reagents that are added to facilitate the release of cells, avoiding the possibility of a potential contaminant remaining in the final cell suspension. As a result, cells with a cell surface marker, e.g., CD31+ cells, isolated using the devices and methods described herein are suitable for direct and immediate administration to a subject without any additional purification or characterization steps.

The aptamer used in the foregoing methods is an aptamer suitable for specifically binding a cell surface marker, e.g., CD31, as described herein. The aptamer can be coupled to the beads in a manner suitable for release of cells with a cell surface marker, e.g., CD3130 cells, in the absence of a chemical agent, and production of a cell population enriched for cells with a cell surface marker, e.g., CD31+ cells, substantially free of beads and aptamer. Interaction between aptamer and beads should be sufficiently strong to allow release of the cells using mechanical force without removing the aptamer from the beads. Accordingly, the strength of the interaction between the aptamer and the beads should be significantly stronger than the strength of the interaction between the aptamer and the target antigen. Such an interaction can be accomplished by non-covalently coupling the aptamer to the beads. For example, the aptamer is non-covalently coupled to the beads through a streptavidin and biotin interaction. The aptamer is biotinylated, the beads are coupled to streptavidin, and the aptamer is coupled to the beads through the interaction of biotin and streptavidin.

Alternatively, the aptamer is coupled to streptavidin, the beads are biotinylated and the aptamer is coupled to the beads through the interaction of biotin and streptavidin. A person skilled in the art will recognize that other moieties can be substituted for streptavidin and retain the binding capacity for biotinylated ligand, e.g., Avidin, NeutrAvidin. In some embodiments, interaction between aptamer and beads can be accomplished by covalently coupling the aptamer to the beads. In some embodiments, the aptamer is present at a concentration of about 1-50 µg/mL, e.g., 10-40 µg/mL, 20-50 µg/mL, 30-50 µg/mL, 5-10 µg/mL, 5-25 µg/mL, or 10-20 µg/mL. In an exemplary embodiment, the aptamer is present at a concentration of 10 µg/mL. Aptamer may be loaded on beads using any art-recognized method. For example, the anti-CD31 aptamer may be attached to the beads by suspending the beads in a aptamer containing solution followed by a 20 minute incubation at 4° C. The aptamer coupled beads can be subsequently collected by centrifugation.

In some embodiments, the methods use a mixture of beads coupled to the aptamer and beads not coupled to the aptamer. The ratios between aptamer-coupled beads and aptamer-free beads used in the methods of the invention include, but not limited to, 1:1, 2:1, 3:1, 4:1, 5:1, 1:2, 1:3, 1:4, and 1:5. In exemplary embodiments, the ratio of aptamer-coupled beads to aptamer-free beads is 1:1, 2:1 or 3:1. In exemplary embodiments, the method can be performed using a device as described herein.

After release from beads, cells with a cell surface marker, e.g., CD31+ cells, can be recovered from the aptamer-coupled beads by passage through a filter having a pore size of, for example, less than 30 µm, less than 25 µm, less than 20 µm, less than 15 µm, or less than 10 µm. Upon passing through the filter, cells can be collected and recovered by centrifugation. In one embodiment, the method is performed in the absence of an antibody specific for a cell surface marker, e.g., an anti-CD31 antibody.

Cells with a cell surface marker, e.g., CD31+ cells, may be enriched and/or isolated from a whole blood sample, a peripheral blood mononuclear cell (PBMC) sample, a bone marrow sample, a hematoma sample, a tissue sample collected at the site of a bone fracture, a fluid sample collected at the site of a bone fracture, or combinations thereof. In some embodiments, the cell population containing cells with and without the cell surface marker, e.g., CD31+ and CD31− cells, is enriched and/or isolated from a blood sample. In other embodiments, the cell population containing cells with and without the cell surface marker, e.g., CD31+ and CD31− cells, is enriched and/or isolated from is a peripheral blood mononuclear cell (PBMC) sample. In some embodiments, the cell population containing cells with and without the cell surface marker, e.g., CD31+ and CD31− cells, is enriched and/or isolated from a tissue sample collected at the site of a bone fracture. In other embodiments, the cell population containing cells with and without the cell surface marker, e.g., CD31+ and CD31− cells, is enriched and/or isolated from a fluid sample collected at the site of a bone fracture, In yet another embodiment, the cell population containing cells with and without the cell surface marker, e.g., CD31+ and CD31− cells, is enriched and/or isolated from a combination of a blood sample, a tissue and/or fluid sample collected at the site of a bone fracture.

In some embodiments it is desirable for the enrichment method described herein to be performed over a short duration of time. Accordingly, in some embodiments, the enrichment method described herein can be performed in 15-60 minutes or less, e.g., 15 minutes or less, 30 minutes or less, 45 minutes or less, or 60 minutes or less. In some embodiments, the enrichment method is performed in 2 hours or less. In an exemplary embodiment, the enrichment method is performed in 30 minutes or less. In one embodiment, the enrichment method is performed during a surgical procedure.

In one embodiment, the method further comprises obtaining the cell sample from a subject. The cell sample can be obtained from the subject using any suitable method. In exemplary embodiments, a blood sample is obtained from the subject. In another embodiment, a tissue sample is obtained from the subject. In another embodiment, a suction sample containing blood and/or tissue is obtained from the subject, e.g., by suction of a site within the subject, e.g., a surgical site, a site of injury, etc. In one embodiment, the cell sample is obtained from the subject prior to a surgical procedure, e.g., less than one hour, within 1 hour, within 2 hours, within 3 hours, within 5 hours, within 10 hours, within 12 hours, within 24 hours of a surgical procedure. In another embodiment, the cell sample is obtained from the subject during surgery.

In one embodiment, the method further comprises administering the enriched or isolated cell population to the subject. The enriched or isolated cell population can be administered to the subject by standard means, to a location within the subject where the enriched cell population is expected to provide a clinical benefit. For example, cells enriched for expression of CD31 can be administered to the site of a bone fracture, where they are expected to facilitate bone healing. In one embodiment, the starting population of cells is obtained from a subject, enriched using the methods described herein, and the enriched population of cells is administered to the subject, during the course of a surgical procedure. For example, a starting population of cells (e.g., a blood sample, etc.) can be obtained from a subject during or shortly before a surgical procedure. The cells can be enriched while the surgical procedure is performed, and the enriched cells can be administered to the subject during the surgical procedure. Accordingly, the cell enrichment method can be performed intraoperatively.

Cells enriched, purified or isolated using the methods described herein are free or substantially free of beads, aptamer, antibody, or any other agents or contaminants. As such, the cell population enriched for cells expressing a cell surface marker have the potential to be administrated directly to a subject, without the need for additional purification steps. For example, the cell population enriched for cells expressing a cell surface marker, e.g., CD31+ cells, can be administered to the subject by introduction at a surgical site. In exemplary embodiments, the cell population enriched for cells expressing a cell surface marker, e.g., CD31+ cells, can be administered to the subject at a site of injury. For example, a cell population enriched for cells expressing a cell surface marker, e.g., CD31+ cells, can be administered at a site that would benefit from angiogenesis and/or osteogenesis, for example, the site of a bone fracture. Other therapeutic applications of the enriched cell population are described herein.

In one embodiment, the invention provides a cell population enriched for cells expressing a cell surface marker of interest, e.g., CD31+ cells, substantially free of beads and/or aptamer, that is obtained by the foregoing methods.

In some embodiments, it is desirable to further enrich a cell population for more than one cell surface markers, as described herein. For example, it may be desirable to enrich a cell population for cells containing CD31 and a second cell surface marker. Enrichment for a second cell surface marker may be performed using a solid support (e.g., beads) coupled to an aptamer which specifically binds the second cell surface marker. Cells bound by the aptamer can be released from the solid support using methods described herein, for example, mechanical disruption. Alternatively, enrichment for a second cell surface marker may be performed using other methods known in the art, for example, antibody-based methods, methods using magnetic beads, etc.

Accordingly, in some embodiments, the methods described herein may further involve enriching a cell population for a second cell surface marker. In one embodiment, enrichment for CD31 and enrichment for a second cell surface marker are performed sequentially. For example, a cell population may be enriched for CD31 using the methods set forth herein, and the CD31+ enriched cell population may then be enriched for the presence of a second cell surface marker. Alternatively, a cell population may be enriched for a second cell surface marker, and the cells enriched for the second cell surface marker can subsequently be enriched for CD31 using the methods set forth herein. Such methods of successive enrichment will produce a cell population enriched for cells that contain both cell surface markers, i.e., cells that express both CD31 and the second cell surface marker.

In other embodiments, enrichment for CD31 and enrichment for a second cell surface marker are performed simultaneously. For example, a cell population may be enriched by binding the cells to a solid support (e.g., beads) which contains an anti-CD31 aptamer and a ligand (e.g., an aptamer) that binds the second cell surface marker. In one embodiment, the cell population is bound to beads that are coupled to an anti-CD31 aptamer and an aptamer that specifically binds the second cell surface marker. In another embodiment, the cell population is bound to beads that are coupled to an anti-CD31 aptamer, mixed with beads that are coupled to an aptamer that binds the second cell surface marker. Such methods of simultaneous enrichment will produce a cell population enriched for cells that contain either antigen, i.e., cells that express either CD31 or the second cell surface marker.

V. Kits

The present invention also provides kits for enrichment of cells with a cell surface marker, e.g., CD31+ cells, from a subject. The kits contain a portable column packed with aptamer-coupled beads, wherein the aptamer is suitable for specifically binding the cell specific marker, e.g., CD31, and wherein the column comprises a filter having a pore size smaller than the diameter of the beads. Kits may further comprise, in some embodiments, instructions for use of the kit to enrich cells with a cell surface marker, e.g., CD31+ cells, from a subject cell sample comprising cells with and without the cell surface marker, e.g., CD31+ and CD31− cells.

A portable column is capable of being transported and can be easily carried or conveyed by hands. In some embodiments, the portable column is prepackaged in a sterile container. A sterile container is free from living germs or microorganisms. A sterile container is aseptic. As such, cells isolated using the kits can be administered to a subject, for example, to the subject from which the non-enriched cell population was derived by introduction at a surgical site. In a an exemplary embodiment, the cell population enriched for cells with a cell surface marker, e.g., CD31+ cells, can be administered to the subject by injection at the site of a bone fraction.

In some embodiments, the portable column is packed with beads and can be of a size and character to allow release of cells without removal of beads. in some embodiment, the column can be of a volume of about 1 mL, 2 mL, 3 mL, 4 mL, 5 mL, 6 mL, 7 mL, 8 mL, 9 mL, 10 mL, 15 mL, 20 mL, 30 mL, 40 mL, 50 mL, 60 mL, 70 mL, 80 mL, 90 mL or 100 mL. When beads are packed in a column, the column can further comprise a filter with pores to allow cells to pass through while retaining beads in a column. In one embodiment, the filter has a pore size smaller than the diameter of the beads. In another embodiment, the filter has a pore size larger than cells to be enriched. In some embodiments, the filter has a pore size of, for example, less than 25 µm, less than 20 µm, less than 15 µm, or less than 10 µm.

In some embodiments, the kit further comprises centrifuge tubes for colleting cells. To facilitate removal of cells with a cell surface marker, e.g., CD31+ cells, from beads, the column can be sized to fit in a centrifuge tube, for example, a small eppendorf tube or a large falcon tube, such that the beads can be collected by centrifugation using either a tabletop centrifuge or a large centrifuge. In other embodiments, the kit further comprises a syringe that is fitted to the column to mechanically disrupt the interaction between beads and cells, and to control the flow rate during the cell enrichment procedure.

In some embodiments, the kit further comprises a mixture of beads coupled to the aptamer and beads not coupled to the aptamer. The ratios between aptamer-coupled beads and aptamer-free beads in the kits of the invention include, but not limited to, 1:1, 2:1, 3:1, 4:1, 5:1, 1:2, 1:3, 1:4, and 1:5. In some embodiments, the ratio of aptamer-coupled beads to aptamer-free beads is 1:1, 2:1 or 3:1. In some embodiment, the bead is larger than a cell. In other embodiments, the beads are larger than the pore size of the filter. In some embodiments, the beads have a diameter of about 30-200 µm. In other embodiments, the beads have a diameter of about 50-150 µm, or a diameter of about 100-150 µm. Alternatively, the beads can have a diameter of about 50 µm, 60 µm, 70 µm, 80 µm, 90 µm, 100 µm, 110 µm, 120 µm, 130 µm, 140 µm and 150 µm.

The kit may contain any standard beads known in the art for cell-based chromatography, for example, agarose beads. Alternatively, the beads are sepharose beads. Another example of the bead is a polystyrene bead, for example, polystyrene beads from the company Spherotech. In an exemplary embodiment, the beads are not magnetic.

In another embodiment, the kit further comprises a resuspension buffer. The resuspension buffer can be any water-based salt solution known in the art that has an osmolarity and ion concentrations that match those of the human body. In one embodiment, the resuspension buffer is phosphate buffered saline (PBS).

Cells with a cell surface marker, e.g., CD31+ cells, isolated using the kits described herein are free or substantially free of beads, aptamer, antibody, or any other reagents that are added to facilitate the release of cells, avoiding the possibility of a potential contaminant remaining in the final cell suspension. As a result, cells with a cell surface marker, e.g., CD31+ cells, isolated using the kits can be used for various purposes. For example, the isolated cells with a cell surface marker, e.g., CD31+ cells, are suitable for direct and immediate administration to a subject without any additional purification or characterization steps. Alternatively, cells with a cell surface marker, e.g., isolated CD31+ cells, are suitable for propagation in a suitable cell culture medium for in vitro studies.

In one embodiment, the instruction states that the prepackaged column is suitable for intraoperative cell enrichment. In another embodiment, the instruction states that the prepackaged column is suitable for a single use. In yet another embodiment, the instruction states that the prepackaged column is disposable.

VI. Methods of Treatment

The present invention also provides methods of cell-based therapy, using a population of cells that has been enriched for cells that express a cell surface marker of interest. In some embodiments, cells expressing the cell surface marker, are administered to a subject in need thereof (e.g., by injection or grafting at a surgical site). In a particular embodiment, the site of administration in the organ or tissue to be augmented is a surgical site. In one embodiment, the enriched cells are CD31+ cells, and the CD31+ cells are administered at or near the site of a bone fracture.

In one embodiment, the method comprises contacting the cell sample with aptamer-coupled beads, wherein the aptamer is suitable for specifically binding a cell surface marker, e.g., CD31; washing the aptamer-coupled beads with a wash buffer such that all or a portion of the cells without the cell surface marker, e.g., CD31− cells, are removed from the cell sample; subjecting the aptamer-coupled beads to a mechanical force sufficient to release the cells with a cell surface marker, e.g., CD31+ cells, from the aptamer-coupled beads; recovering the cells with a cell surface marker, e.g., CD31+ cells, from the aptamer-coupled beads; such that the recovered cells with a cell surface marker, e.g., CD31+ cells, are substantially free of beads and/or aptamer; and introducing the recovered cells with a cell surface marker, e.g., CD31+ cells, at a surgical site in a subject. Alternatively, the method comprises administering to a subject in need thereof a cell population enriched for cells with a cell surface marker, e.g., CD31+ cells, that are substantially free of beads, aptamer, antibody, and/or nuclease by introducing the cells with a cell surface marker, e.g., CD31+ cells, at a surgical site in a subject. In some embodiments, the method is performed intraoperatively. In other embodiments, the method is performed perioperatively or postoperatively.

Cells with a cell surface marker, e.g., CD31+ cells, may be enriched and/or isolated from a whole blood sample, a peripheral blood mononuclear cell (PBMC) sample, a bone marrow sample, a hematoma sample, a tissue sample collected at the site of a bone fracture, a fluid sample collected at the site of a bone fracture, or combinations thereof. In some embodiments, the cell population containing cells with and without the cell surface marker, e.g., CD31+ and CD31− cells, is enriched and/or isolated from a blood sample. In other embodiments, the cell population containing cells with and without the cell surface marker, e.g., CD31+ and CD31− cells, is enriched and/or isolated from is a peripheral blood mononuclear cell (PBMC) sample. PBMC can be obtained from whole blood using methods known in the art, for example, density centrifugation. In some embodiments, the cell population containing cells with and without the cell surface marker, e.g., CD31+ and CD31− cells, is enriched and/or isolated from a tissue sample collected at the site of a bone fracture. In other embodiments, the cell population containing cells with and without the cell surface marker, e.g., CD31+ and CD31− cells, is enriched and/or isolated from a fluid sample collected at the site of a bone fracture, In yet another embodiment, the cell population containing cells with and without the cell surface marker, e.g., CD31+ and CD31− cells, is enriched and/or isolated from a combination of a blood sample and a tissue and/or fluid sample collected at the site of a bone fracture, In yet a further embodiment, the method comprises obtaining the cell sample from a subject using any of the well known methods in the art.

The methods provided herein are useful in applications including, but not limited to, promoting angiogenesis, promoting osteogenesis, promoting immunomodulation, and/or treating bone fractures. Diseases that may be treated with the methods disclosed herein include, but are not limited to, angiogenesis-related diseases, osteogenesis-related diseases, immunomodulation-related diseases, and bone fracture. "Treat" refers to any type of treatment that imparts a benefit to a patient, e.g., a patient afflicted with or at risk for developing a disease. Treating includes actions taken and actions refrained from being taken for the purpose of improving the condition of the patient (e.g., the relief of one or more symptoms), delay in the onset or progression of the disease, etc.

As defined herein, "angiogenesis-related diseases" are those diseases benefiting from promoting angiogenesis, and include, but are not limited to, ischemic vascular disease, diabetic retinopathy, retinopathy of prematurity, age-related macular degeneration, glaucoma, diabetic foot ulcer, pulmonary hypertension, ischemic cardiomyopathy, ischemic brain disease, heart failure, acute posterior ischemia, or obesity-related cardiovascular disease.

"Osteogenesis-related diseases" are those diseases benefiting from promoting osteogenesis, and include, but are not limited to, osteoporosis, hypercalcemia, Paget disease, and neoplastic bone destruction.

"Bone-fracture" can be the result of trauma or due to some other underlying cause that leads to a weakening of the bones or bone loss. Conditions that lead to a weakening of the bones or bone loss include, but are not limited to, osteoporosis, rheumatoid arthritis (RA), lupus, multiple sclerosis, ankylosing spondylitis, celiac disease, inflammatory bowel disease (IBD), weight loss surgery (e.g., gastrectomy, gastrointestinal bypass procedures), diabetes, hyperparathyroidism, hyperthyroidism, Cushing's syndrome, thyrotoxicosis, low estrogen levels in women, premature menopause, abnormal testosterone and estrogen levels in men, leukemia and lymphoma, multiple myeloma, sickle cell disease, blood and bone marrow disorders, thalassemia, stroke, Parkinson's disease, multiple sclerosis (MS), spinal cord injuries, depression, eating disorders (e.g., anorexia nervosa, bulima nervosa, and the like), breast cancer, prostate cancer, AIDS/HIV, chronic obstructive pulmonary disease (COPD), female athlete triad, kidney disease, liver disease, organ transplants recipients, polio and post-polio syndrome, poor diet (e.g., malnutrition), scoliosis, and weight loss.

"Immunomodulation-related diseases" are those disease benefiting from promoting immunomodulation, and include, but are not limited to, rheumatoid arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis scleroderma, graft versus host disease, organ transplant rejection, acute or chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic, polyglandular deficiency type I and polyglandular deficiency type II, Schmidt's syndrome, adult (acute) respiratory distress syndrome, alopecia, alopecia greata, seronegative arthopathy, arthropathy, Reiter's disease, psoriatic arthropathy, ulcerative colitic arthropathy, enteropathic synovitis, *chlamydia, yersinia* and *salmonella* associated arthropathy, spondyloarthopathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free Disease, chronic mucocutaneous candidiasis, giant cell arteritis, primary sclerosing hepatitis, cryptogenic autoimmune hepatitis, Acquired Immunodeficiency Disease Syndrome, Acquired Immunodeficiency Related Diseases, Hepatitis B, Hepatitis C, common varied immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjogren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classical autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, acute immune disease associated with organ transplantation, chronic immune disease associated with organ transplantation, osteoarthrosis, primary sclerosing cholangitis, psoriasis type 1, psoriasis type 2, idiopathic leucopaenia, autoimmune neutropaenia, renal disease NOS, glomerulonephritides, microscopic vasulitis of the kidneys, lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjorgren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo acute liver disease, chronic liver diseases, alcoholic cirrhosis, alcohol-induced liver injury, choleosatatis, idiosyncratic liver disease, Drug-Induced hepatitis, Non-alcoholic Steatohepatitis, allergy and asthma, group B streptococci (GBS) infection, mental disorders (e.g., depression and schizophrenia), acute and chronic pain (different forms of pain), and cancers such as lung, breast, stomach, bladder, colon, pancreas, ovarian, prostate and rectal cancer and hematopoietic malignancies (leukemia and lymphoma), Abetalipoprotemia, Acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, aerial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti cd3 therapy, antiphospholipid syndrome, anti-receptor hypersensitivity reactions, aordic and peripheral aneuryisms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, Burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chromic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, Dementia pugilistica, demyelinating diseases, dengue hemorrhagic fever, dermatitis, dermatologic conditions, diabetes, diabetes mellitus, diabetic ateriosclerotic disease, Diffuse Lewy body disease, dilated congestive cardiomyopathy, disorders of the basal ganglia, Down's Syndrome in middle age, drug-induced movement disorders induced by drugs which block CNS dopamine receptors, drug sensitivity, eczema, encephalomyelitis, endocarditis, endocrinopathy, epiglottitis, epstein-barr virus infection, erythromelalgia, extrapyramidal and cerebellar disorders, familial hematophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallerrorden-Spatz disease, hashimoto's thyroiditis, hay fever, heart transplant rejection, hemachromatosis, hemodialysis, hemolytic uremic syndrome/thrombolytic thrombocytopenic purpura, hemorrhage, hepatitis (A), His bundle arrythmias, HIV infection/HIV neuropathy, Hodgkin's disease, hyperkinetic movement disorders, hypersensitity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, Asthenia, infantile spinal muscular atrophy, inflammation of the aorta, influenza a, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, *legionella*, leishmaniasis, leprosy, lesions of the corticospinal system, lipedema, liver transplant rejection, lymphederma, malaria, malignant Lymphoma, malignant histiocytosis, malignant melanoma, meningitis, meningococcemia, metabolic/idiopathic, migraine headache, mitochondrial multisystem disorder, mixed connective tissue disease, monoclonal gammopathy, multiple myeloma, multiple systems degenerations (Mencel Dejerine-Thomas Shi-Drager and Machado-Joseph), myasthenia gravis, *mycobacterium avium intracellulare, mycobacterium tuberculosis*, myelodyplastic syndrome, myocardial infarction, myocardial ischemic disorders, nasopharyngeal carcinoma, neonatal chronic lung disease, nephritis, nephrosis, neurodegenerative diseases, neurogenic I muscular atrophies, neutropenic fever, non-Hodgkin's lymphoma, occlusion of the abdominal aorta and its branches, occlusive arterial disorders, okt3 therapy, orchitis/epidymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, Progressive supranucleo Palsy, primary pulmonary hypertension, radiation therapy, Raynaud's phenomenon and disease, Raynaud's disease, Refsum's disease, regular narrow QRS tachycardia, renovascular hypertension, reperfusion injury, restrictive cardiomyopathy, sarcomas, scleroderma, senile chorea, Senile Dementia of Lewy body type, seronegative arthropathies, shock, sickle cell anemia, skin allograft rejection, skin changes syndrome, small bowel transplant rejection, solid tumors, specific arrythmias, spinal ataxia, spinocerebellar degenerations, streptococcal myositis, structural lesions of the cerebellum, Subacute sclerosing panencephalitis, Syncope, syphilis of the cardiovascular system, systemic anaphalaxis, systemic inflammatory response syndrome, systemic onset juvenile rheumatoid arthritis, Telangiectasia, thromboangitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, vital encephalitis/aseptic meningitis, vital-associated hemaphagocytic syndrome, Wernicke-Korsakoff syndrome, Wilson's disease, and xenograft rejection of any organ or tissue.

In exemplary embodiments, the enriched cells expressing a cell surface marker, e.g., CD31+ cells, described herein are useful for treating ischemic diseases, vascular diseases, or bone regeneration. Such disorders are described herein, and are further described in, for example, Soltan, M., et al., *Implant Dent.* 21, 13 (2012); Dong, L., et al., *Trends Biotechnol.* 31, 342-6 (2013); Simari, R. et al., *J. Am. Coll. Cardiol.* 56,608-9 (2010); and Kim, S.-W. et al., *Journal of the American College of Cardiology* (2010).

The enriched cells that express a cell surface marker, e.g., CD31+ cells, used in the methods provided herein may be mixed with or seeded onto a pharmaceutically acceptable carrier prior to administration. "Pharmaceutically acceptable" means that the compound or composition is suitable for administration to a subject to achieve the treatments described herein, without unduly deleterious side effects in light of the severity of the disease and necessity of the treatment. Such formulations can be prepared using techniques well known in the art. See, e.g., U.S. Patent Application 2003/0180289; Remington: *The Science and Practice of Pharmacy*, Alfonso R. Gennaro, editor, 20th ed. Lippincott Williams & Wilkins: Philadelphia, Pa., 2000. The carrier may be a solid or a liquid, or both (e.g., hydrogels), and can be formulated with the cells as a unit-dose formulation. In some embodiments the cells are provided as a suspension in the carrier to reduce clumping of the cells. In other embodiments cells are seeded onto a biodegradable scaffold or matrix. A "biodegradable scaffold or matrix" is any substance not having toxic or injurious effects on biological function and is capable of being broken down into is elemental components by a host. The scaffold or matrix may be porous to allow for cell deposition both on and in the pores of the matrix. Such formulations can be prepared by supplying at least one cell population to a biodegradable scaffold to seed the cell population on and/or into the scaffold. The seeded scaffold may then implanted in the body of a recipient subject.

Formulations of the invention include those for parenteral administration (e.g., subcutaneous, intramuscular, intradermal, intravenous, intraarterial, intraperitoneal, percutaneous injection) by injection or implantation. In one embodiment, administration is carried out intravascularly, either by simple injection, or by injection through a catheter positioned in a suitable blood vessel, such as a renal artery. In some embodiments, administration is carried out by "infusion", whereby compositions are introduced into the body through a vein (e.g., the portal vein). In another embodiment, administration is carried out as a graft to an organ or tissue to be augmented as discussed above, e.g., kidney, liver, or a bone-fracture site etc.

In some embodiments, the cells with a cell surface marker, e.g., CD31+ cells, are administered by injection of the cells (e.g., in a suitable carrier) directly into the tissue or organ of a subject that is in need of augmentation (e.g., at a surgical site). For example, cells may be injected into the kidney, liver, or a bone-fracture site. The functional effects of the cells with a cell surface marker, e.g., CD31+ cells, will be systemic, and the cells with a cell surface marker, e.g., CD31+ cells, may therefore be administered by injection into other organs or tissues in proximity to that to be augmented.

According to some embodiments, the cells administered to the subject may be syngeneic (i.e., genetically identical or closely related, so as to minimize tissue transplant rejection), allogeneic (i.e., from a non-genetically identical member of the same species) or xenogeneic (i.e., from a member of a different species), as above, with respect to the subject being treated. Syngeneic cells include those that are autogeneic (i.e., from the subject to be treated) and isogeneic (i.e., a genetically identical but different subject, e.g., from an identical twin). In a preferred embodiment, the cells are autogenetic. Cells also may be obtained from, e.g., a donor (either living or cadaveric) or derived from an established cell strain or cell line. As an example of a method that can be used to obtain cells from a donor (e.g., a potential recipient of a bioscaffold graft), standard biopsy techniques known in the art may be employed. Alternatively, cells may be harvested from the subject, expanded/selected in vitro, and reintroduced into the same subject (i.e., autogenic).

In some embodiments, cells are administered in a therapeutically effective amount. The therapeutically effective dosage of cells will vary somewhat from subject to subject, and will depend upon factors such as the age, weight, and condition of the subject and the route of delivery. Such dosages can be determined in accordance with procedures known to those skilled in the art. In general, in some embodiments, a dosage of $1\times10^5$, $1\times10^6$ or $5\times10^6$ up to $1\times10^7$, $1\times10^8$ or $1\times10^9$ cells or more per subject may be given, administered together at a single time or given as several subdivided administrations. In other embodiments, a dosage of between $1-100\times10^8$ cells per kilogram subject body weight can be given, administered together at a single time or given as several subdivided administration. If necessary, subsequent, follow-up administrations also may be given.

Cells may be administered according to some embodiments to achieve a target hematocrit range. The ideal or target hematocrit range may vary from subject to subject, depending upon, e.g., specific comorbidities. In some embodiments the target hematocrit is from 30-40%, in some embodiments the target hematocrit is from 33-38%, and in some embodiments the target hematocrit is from 33-36%. Upon administration of cells according to the present invention, hematocrit may be measured and, if desired or necessary, corrected by, e.g., further implantation of cells and/or other methods known in the art. Other methods of treatment for promoting angiogenesis, promoting osteogenesis, promoting immunomodulation, and treating bone fracture may be used in conjunction with the methods of treatment provided herein, for example, other cell-based therapies, other angiogenesis promoting agents, other osteogenesis promoting agents, other immunomodulation promoters, and other bone fracture treatments.

The invention is further described in the following examples, which do not limit the scope of the invention described in the claims.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

EXAMPLES

Materials and Methods

PBMC Preparation

For the initial studies, peripheral blood mononuclear cells (PBMCs) were obtained from apheresis leukoreduction filters using traditional density centrifugation method. The Brigham and Women's hospital specimen bank provided the samples from consented patients. The cell suspension was diluted with Dulbecco's phosphate buffered saline (PBS) 1:1 before being layered onto density centrifugation medium (Ficoll-paque plus, VWR, #17-1440-02) and centrifuged for 30 min at 400 g without brake. The PBMCs layer was aspirated and rinsed twice at 200 g for 8 min to remove platelets. PBMCs were then used for subsequent aptamer validation or frozen for system optimization experiments. For magnetic bead studies and system validation, fresh whole blood samples were purchased from Research Blood Components (Boston, Mass.) and diluted with an equal volume of PBS+2% fetal calf serum. PBMCs were obtained by following the manufacturer's instruction with the Sepmate procedure (Stem Cell Technologies, #15460).

Aptamer Specificity

A commercially available biotinylated aptamer for CD31 was purchased (APTSCI, #CD31-2196BCI). To validate its specificity, PBMCs were resuspended at a concentration of $10^7$ cells/ml. 100 µl of cells were incubated with the biotinylated aptamer at different concentrations for 30 min at 4° C. Cells were then centrifuged for 5 min at 1200RPM and resuspended in 100 µl flow cytometry staining buffer (eBioscience, #00-4222-26). Cells were stained for CD31 (Alexa fluor 488, CD31, Biolegend, #303110) and biotin (PE antibiotin antibody, Biolegend, #409004) before being analyzed on a BD LSRFortessa with HTS.

Magnetic Bead Studies

To benchmark the new approach, established and commercially available bead sorting strategies were used as comparison. In certain studies, CD31+ cells were isolated by immunomagnetic cell separation (MACS System; Milteny Biotec) according to the manufacturer's instruction using the CD31 Microbead kit (Milteny Biotec, #130-091-935). For the aptamer, magnetic cell sorting was performed using a cell isolation kit for CD31+ cells (APTSCI, #CD31-2196BCI) and following the manufacturer's instruction.

In Vitro Characterization: Flow Cytometry Analysis

In order to analyze the different populations, cells were resuspended in flow cytometry staining buffer at $10^7$ cells/ml and stained for CD14 (Biolegend, #325628), CD45 (Biolegend, #304006), CD31 (Biolegend, #303116), CD3 (Biolegend, #300308) and CD19 (Biolegend, #302208) and analyzed on BD LSRFortessa. For all analysis, the initial gating on PBMCs was performed using FSC and SSC parameters. Subsequently, CD31+ levels were analyzed. For the CD31+ cells composition, gating was performed on CD31+ cells and composition with regards to monocytes (CD14+), T cells (CD3+) and B cells (CD19+) was evaluated.

System Assembly

A tube based system was developed for cell enrichment. Microcentrifuge tubes (Pierce, #69705) served as the basis for the system. Using tweezers, polyethylene filters were removed from the tubes. Then, biopsy punches (Sklar Instruments, #96-115) were used to extract 4 mm diameter filters from 20 um cell strainers (Pluriselect, # 43-50020-03). A thin layer of cyanoacrylate glue (E-Z bond, #S-105) was applied to the base of the microcentrifuge tubes. The punched-out filter was then applied to the base of the tube and pressed slightly using tweezers. The system was then left to dry overnight at room temperature. Neutravidin agarose beads were packed within the tube: neutravidin agarose beads (Piercenet, #29204) were diluted in PBS with calcium and magnesium and filtered through a 100 µm filter (Falcon, #352360). Remaining beads in the filter were then collected. The beads solution was allowed to settle before being resuspended in PBS. After a quick centrifugation step (1 min, 300 g), beads were resuspended in a solution of biotinylated aptamers and incubated for 20 min at 4° C. After incubation, the tube was centrifuged and washed twice in PBS to remove unbound aptamer. Two additional rinsing steps were performed before finally resuspending in 600 µl of binding buffer (APTSCI, #CD31-2196BCI) and transferring beads to the tube. In certain studies, unmodified and aptamer coated beads were mixed and used in the columns. Luer-lock adaptors allowed these columns to be used with BD biosciences syringes.

Isolation Procedure: From PBMCs to CD31+ Enriched Cell Population

The PBMCs were run through the enrichment system at 50 µl/min, at a concentration of 2.5×10⁷ cells/ml in binding buffer for 10 min. During that step, the whole system was kept vertical during the duration of the experiment to alleviate issues related to cell sedimentation due to the small diameter of 1ml syringes. Another 500 µl of binding buffer was then run through at the same speed, before rinsing using 3 ml of PBS at 300 µl/min to remove unbound cells. An infusion syringe pump was used to control the flow-rate (Braintree Scientific, #BS300). The system was then disconnected from the syringe and beads were resuspended by sucking in and out of 1 ml syringe with an 18GA needle (VWR, KT868280-1801). This approach dispersed the beads in solution and resulted in the release of the cells. The tube was centrifuged in a 2 ml eppendorf tubes at 300 g for 3 min to collect the released cell population. Cell viability was measured using the Muse® Cell Analyzer.

Conditioned Medium Studies

Conditioned medium from the initial PBMCs population and released cell population was prepared to assess their angiogenic and osteogenic potential. Cells were cultivated in EBM basal medium (Lonza, #CC3121) supplemented with 10% fetal calf serum and 1% penicillin/streptomycin (Biochrome) for the former and in DMEM low Glucose (Sigma-Aldrich) supplemented with 10% fetal calf serum and 1% penicillin/streptomycin (Biochrome) for the latter. 1.2×10⁶ cells were kept in 6 ml of medium over 24 hours. The medium was then sterile filtered and stored at −20° C. until further experiments.

In-Vitro: Angiogenic Potential

The angiogenic potential of the cells was assessed using a tube formation assay. 96-well plates were coated with 50 µl/well of Matrigel growth factor reduced (VWR, #354230) and transferred to a 37° C. cell culture incubator to allow the gel to solidify. In the meantime, a single cell suspension of human umbilical vein endothelial cells (HUVECS, Lonza, #CC2519) between passage 3 and 5, at 2×10⁵cells/ml was prepared. 50 µl of the cell suspension was added to each well in culture medium without angiogenesis activators or inhibitors. Cells were allowed to adhere for 20 minutes before adding 150 µl of conditioned medium. The plate was then incubated overnight. Networks of cell structures were examined under a microscope and images were taken at 10×. The total length of the network per image was evaluated using ImageJ and divided by the results obtained for the HUVECS cultured in culture medium without angiogenesis activators or inhibitors. For a positive control, the EGM bullet kit was used (Lonza, #CC3124).

In-Vitro: Osteogenic Potential

Mesenchymal stromal cells were purchased from ATCC (#PCS-500-012). Cells from passage 3-4 were used for the experiments. In brief, 2.4×10⁴ cells per well were seeded in a 96 well-plate and cultivated in expansion medium for 24 hours before induction. Commercially available osteogenic differentiation medium (LifeTechnologies, #A10072-01) was purchased and diluted 1:1 with conditioned media and 100 µl medium were applied to each well with biweekly medium exchange. At the end of the study cell proliferation was evaluated using a redox-based metabolic assay (AlamarBlue Cell Viability Reagent, LifeTechnologies), and the osteogenic differentiation visualized via Alizarin Red S staining (ARS). The stained wells were rinsed repeatedly with PBS. Then, matrix-bound ARS was dissolved by addition of 10% cetylpyridinium chloride before measuring absorption at 562 nm. The resulting values were normalized to the values obtained from alamar blue and divided by the values of the control cell group cultured in regular osteogenic differentiation medium.

Example 1

Aptamer Selection and Validation

A 2D cell adhesion assay was performed to examine the capacity of different ligands to capture and release CD31+ cells. Three different ligands were investigated: an anti-CD31 antibody (Biolegend, 27333), recombinant human integrin αβf3 (R&D systems, 3050-AV-050), and a commercially available aptamer (Aptamer Sciences Inc., Pohang, Gyoungbuk, South Korea). To optimize the ligand concentration, five different concentrations of each ligand were tested, including 0 µg/mL, 0.1 µg/mL, 1 µg/mL, 5 µg/mL and 10 µg/mL. Each ligand was coated on Maxisorp 96 well plate (Nunc, 442404) at the desired concentration by passive adsorption and incubated over night at 4° C. Two washes were performed using PBS before blocking with 0.2% Pluronic F-127 (89139-290) for one hour at 37° C. The plate was then rinsed twice using 200 µL PBS before adding peripheral blood mononuclear cells at 5×10⁴ cells/well. The plate was incubated for one hour at 4° C. and then 30 min at 37° C. 200 µL of room temperature PBS was added to each well using a syringe pipette, and buffer was aspirated to remove non-adherent cells from well. Care was taken to leave approximately 50 µL in the plate to not disturb the adherent cells. The washes were repeated three times. Subsequently, cells were fixed for 30 min in 4% PFA before being stained with DAPI (Biolegend, 422801). Pictures were taken under 10× magnification using an Evos® FL inverted microscope. Cell counting was performed using Image J to extract adherent cell density.

As shown in FIG. 2A, without blocking agent, cells can adhere to the Maxisorp 96 well plate. However, pluronic F-127 prevented cell adhesion almost completely. Increasing the concentration from 0.1 to 10 µg/mL resulted in an increase in the amount of cells captured. All three different ligands showed a saturation of cell density at 5 µg/ml. Therefore, this value was used to analyze the purity of non-adherent (NA) and released (R) cell populations.

For cell release, the same procedure as described before was used until the washing steps. During the washing steps, all non-adherent cells were collected. For each experiment, cells from 12 wells were combined to obtain a sufficient number of cells for staining. Released cells (R) cells were collected when pipetting the whole volume of the well four times. Resuspension took place in the absence of any chemical agents that would facilitate the release of cells from the ligands, such as nucleases, and was done using PBS. Non-adherent (NA) and released (R) cells were then stained for CD31 (Alexa fluor 488 CD31 (Biolegend, 303110) and quantified using flow cytometry. CD31 levels in NA cells and R cells are summarized in FIG. 2B. As shown in FIG. 2B, there was a decrease in the number of CD31+ non-adherent cells in wells coated with the aptamer ligand. A corresponding increase in the level of CD31+ cells was observed in the released fraction in wells containing the anti-CD31 aptamer ligand, indicating that the anti-CD31 aptamer specifically bound CD31+ cells, and indicating that the CD31+ cells were released upon application of mechanical force through resuspension. An anti-CD31 antibody had a greater capacity for capturing cells relative to the aptamer, however, it was not possible to detach CD31+ cells from the anti-CD31 antibody-coated wells using mechanical force.

In order to validate the specificity of the CD31 aptamer, PBMCs were resuspended at a concentration of $10^7$ cells/ml. 100 µl of cells were incubated with the biotinylated version of aptamer for 30 min at 4° C. Cells were then centrifuged for 5 min at 1200 RPM and suspended in 100 µL flow cytometry staining buffer (ebioscience, 00-4222-26). Cells were stained for CD31+ (Alexa fluor 488 CD31 (Biolegend, 303110) and biotin (PE anti-biotin antibody) before being analyzed on BD LSRFortessa. Raw data can be observed on FIG. 2C as well as quantification. Data showed that the aptamer was highly specific for the CD31 population (94.4±3.5 to 97.1±4.3% of the aptamer marked cells were CD31+ positive for the different concentration of aptamer used), with the sensitivity going up to 99.0±1.3% for an aptamer concentration of 5 µg/ml (FIG. 2D). In addition, the specificity was also high with values between 96.9±4.1% and 87.9±4.8 for aptamer concentration of 0.5 µg/ml and 5 µg/ml respectively (FIG. 2D). Also, at a concentration high enough, most of the CD31+ cells were marked (at 5 µg/ml only 1.9±2.2% of CD31+ remained unlabeled, FIG. 2C).

To finish validating the aptamer, its capacity to concentrate CD31+ cells from a population containing a mixture of CD31 positive and negative cells was evaluated. The aptamer was coated onto magnetic beads (Ø=1 um) according to the procedure described in the magnetic isolation kit provided by APTSCI to allow capture of CD31+ cells from peripheral blood mononuclear cells (PBMCs). For this, peripheral blood mononuclear cells were isolated from 100 mL whole blood samples using density centrifugation method (Ficoll-Paque plus). The blood was diluted with Dulbecco's phosphate buffered saline (PBS) and centrifuged for 30 min at 400 g without brake. The PBMCs layer was aspirated and rinse twice at 200 g for 8 min to get rid of most platelets.

Results were benchmarked to a classical magnetic isolation beads approach from MACS technologies (CD31 Microbead kit, Milteny biotec, 130-091-935, FIG. 2E). The aptamer-based isolation and commercial antibody isolation resulted in similar enrichment of CD31+ cells. In both cases, a high enrichment of CD31+ cells was observed (initial population Cd31+ levels: 69±8%, after aptamer-based isolation: 91±10%, after MACS isolation: 99.7±0.1%)

Example 2

Development of a CD31+ Cell Enrichment System

A general outline of the system is as follows: PBMCs that contains a mixture of CD31− and CD31+ cells were run through the system. The CD31+ cells adhered to the aptamer coated beads while CD31− flowed through and were discarded. CD31+ cells were then released from beads with a syringe by imposing fluid shear with a simple mixing of the beads with attached cells and additional medium. Cells released were then collected by centrifugation (FIG. 3A).

System Characteristics

Microcentrifuge tubes (Pierce, #69705) served as a basis. Using tweezers, polyethylene filters were removed from the tubes. Then, biopsy punches (Sklar Instruments, 96-115) were used to obtain 4 mm diameter filters from a 20 µm cell strainer (Pluriselect).

Filters were then glued to the base of the tubes and let to dry overnight at room temperature. Neutravidin agarose beads (Piercenet, #29204) were packed within the tube and coated with a CD31 aptamer (Aptamer Sciences Inc., Pohang, Gyoungbuk, South Korea). Filtering of the neutravidin agarose beads through 100 µm cell strainer makes it impossible for the beads once packed in the tube to go through the 20 µm filter attached. Luer-lock adaptors allowed these columns to be used with BD biosciences syringes (1 ml and 3 ml syringes). Flow-rate was controlled by placing the syringe on an infusion syringe pump (Braintree Scientific, BS300). The whole system was kept vertical during the duration of the experiment to avoid issues related to cell sedimentation.

Enrichment Procedure: From PBMCs to a CD31+ Enriched Cell Population

To prepare the bead suspension, 800 µl of neutravidin agarose beads (Piercenet, #29204) were diluted in 10 ml of PBS with calcium and magnesium. In order to only keep the larger beads, the suspension was then filtered through a 100 µm filter (Falcon, #352360). Beads were collected by turning around the filter on a new 50 ml flacon tube and rinsing with 10 ml of PBS. The procedure was repeated twice. The resulting bead solution was divided into two tubes and allowed to settle down for 10 minutes before being resuspended in 600 µl of PBS. The beads from one tube were transferred to the modified centrifugation tube. After a quick centrifugation step (1 min, 300 g), beads were resuspended in 200 µl of aptamer solution (5 µg/ml, Aptamer Sciences Inc.). The tube was incubated for 20 min at 4° C. After incubation, the tube was centrifuged to remove aptamer solution, and uncoated beads from the second tube were mixed with the aptamer coated beads. Another quick centrifugation was performed and beads were resuspended in 600 µl binding buffer before closing the tube.

As illustrated in FIG. 3A, peripheral blood mononuclear cells (PBMCs) were run through the system to eliminate CD31− cells. For the optimization of the system (FIGS. 3B-3E), cryopreserved PBMCs were used and thawed for every experiment. The PBMC cell suspension was run at 50 µl/min using a concentration of $2.5 \times 10^7$ cells/min in binding buffer, for 10 min. 500 µl of binding buffer was then run through the system at the same speed before rinsing with PBS at 300 µl/min to further remove unbound cells. Cells were released by resuspending the beads with a 1 ml syringe using an 18GA needle (VWR, KT868280-1801 (PK). The released cells were then collected in a 2 ml eppendorf tube by an immediate centrifugation at 300 g for 3 min.

Optimization of the concentration of the aptamer was performed to improve yield without affecting cell viability. As demonstrated in FIG. 3B, the yield of CD31+ cells increased as the concentration of aptamer used to coat the beads increased. A small number of cells remained strongly attached to the beads and required addition of DNAse 1 to release them (FIG. 3B). In general no significant difference was observed between the initial cell viability and that of flow-released cells (FIG. 3C). However, at the highest aptamer concentration, flow-based separation did result in a decrease in cell viability after release, likely due to the overall stronger avidity between the cells and these beads. To determine if adherent cells were retained after intended release, DNAse 1 was applied to digest aptamers after flow release. The use of DNAse 1 significantly affected cell viability at all conditions and increasing aptamer concentration led to an increase of retained cells (FIGS. 4A and 4B). Importantly, the flow based release strategy resulted in an enrichment of CD31+ cells at a lower aptamer concentration but not at the highest aptamer concentrations (FIGS. 4A and 4B). When the concentration of aptamer becomes too high (>10 µg/ml), more than 10% of the cells remain strongly attach to the beads, and the viability of the cells can be affected when resuspending them. Therefore, subsequent steps for optimization were performed using aptamer concentrations of 5 µg/ml and 10 µg/ml, as these provided an appropriate compromise between cell yield, CD31+ purity and cell viability.

The next set of studies explored the impact of combining uncoated and aptamer coated beads, and varying the total bead number in the columns. A mixture of uncoated beads and aptamer coated beads was employed in the columns, to avoid the potential for clogging the system when all the beads of the system are coated with aptamer. To facilitate release and prevent potential clogging a combination of aptamer coated and uncoated beads was used. Bead number was also optimized. A combination of aptamer coated and uncoated beads in a 1:1 ratio prevented clogging of the system, and no significant difference was observed between the 5 µg/ml and 10 µg/ml concentration in that case (FIG. 3D). Therefore, for validation of the system, a concentration of 5 µg/ml with a 1:1 ratio of uncoated beads to coated beads was chosen. With the 50:50 mix, clogging was no longer observed, avoiding issues related to pressure building-up in the system. The incorporation of uncoated beads also facilitated resuspension of the beads during the cell recovery.

The final parameter optimized was the bead volume. An increasing cell yield was initially obtained as the bead number was increased, until a saturation behavior was observed at 400 µl of bead volume and above (FIG. 3E). The highest yield was achieved when 800 µl of beads (400 µl aptamer coated beads and 400 µl uncoated beads) were added during the enrichment procedure. Importantly, microscopy-based observation of the cell population enriched with this system revealed that none of the isolated cells contained bound beads.

The foregoing parameters can be adjusted as described above to optimize operating conditions use with different aptamers.

Example 3

CD31+ Enriched Cell Populations

To validate the system for enrichment of CD31+ cells from a mixed cell population, fresh whole blood samples were collected and analyzed. Peripheral blood mononuclear cells were isolated from whole blood samples using density centrifugation in Septmate tubes (Stem Cell technologies, 15460). Tubes of this type facilitate performing the procedure in a short amount of time (20 to 30 min), compared to an hour or more with traditional density centrifugation, and eliminates the need for slow density gradient layering. Briefly, whole blood samples were diluted in PBS+2% FCS. Density gradient medium was added to Sepmate tubes before adding diluted blood samples and centrifuging for 10 min at 1200 g at room temperature with brake. The top layer containing the enriched mononuclear cells was poured off and washed twice with PBS+2% FCS and centrifuging at 120 g for 8 min to remove platelets. To prepare the bead suspensions, 800 µl of neutravidin agarose (Piercenet, #29204) were diluted in 10 ml of PBS with calcium and magnesium. In order to only keep the larger beads, it was then filtered through a 100 µm filter (Falcon, #352360). Beads were collected by turning around the filter on a new 50 ml flacon tube and rinsing with 10 ml of PBS. The procedure was repeated twice. The resulting bead solution were divided into two tubes and allowed to settle down for 10 minutes before being resuspended in 600 µl of PBS. One tube was used and the beads were transferred to the modified centrifugation tube. After a quick centrifugation step (1 min, 300 g), beads were resuspended at 200 µl CD31 aptamer solution (5 µg/ml, APTSCI). The tube was closed and incubated for 20 min at 4° C. After incubation, the tube was centrifuged to remove aptamer solution and remaining beads were mixed with the aptamer coated beads. Another quick centrifugation was performed and beads were resuspended in 600 µl binding buffer before closing the tube.

The cells were run through at 50 µl/min using a concentration of $2.5 \times 10^7$ cells/min in binding buffer for 10 min. Another 500 µl of binding buffer at the same speed were then run through before rinsing using 3 mls of PBS at 300 µl/min to remove unbound cells. Tube was disconnected from the syringe and beads were resuspended using a 1 ml syringe with an 18GA needle (VWR, KT868280-1801 (PK)). The released cells were collected by placing the tube in a 2 ml eppendorf tubes and immediate centrifugation at 300 g for 3 min.

In order to analyze the different populations obtained and level of enrichment, cells were resuspended in 100 ul flow cytometry staining buffer (00-4222-26) at $10^7$ cells/ml and stained for CD14 (Biolegend 325628), CD45 (Biolegend 304006), CD31 (Biolegend 303116), CD42b (303906), CD3 (Biolegend 300308) and CD19 (Biolegend 302208) and analyzed on BD LSRFortessa. The gating of PBMCs was performed using FSC and SSC parameters before analyzing the composition of the CD31+ fraction.

As shown in FIG. 5A, the system led to a significant enrichment of CD31+ cells from PBMCs (initial population: 65±10%, released: 88±4%) without affecting cell viability (released: 97±2%). The composition of the CD31+ cell fraction before and after isolation also showed an enrichment in monocytes (CD31+CD14+) from 28% to 49% (FIG. 5B), as compared to the initial PBMC population.

Example 4

Angiogenic and Osteogenic Potential of CD31+ Enriched Cell Populations

CD31+ cells have been shown to promote angiogenesis and osteogenesis. To determine whether the enriched CD31+ cells obtained using the optimal column conditions set forth in Example 2 maintain these key functions, both osteogenic and angiogenic in vitro assays were performed. The angiogenic potential of the cells was assessed using a tube formation assay. 40 µl of Matrigel growth factor reduced (VWR, 354230) was used to coat the wells of a 96 well plate. The coated plate was transferred to a 37° C. cell culture incubator for 30 min to allow the gel to solidify. In the meantime, a single cell suspension of $2 \times 10^5$ cells/ml in culture medium without angiogenesis activators and inhibitors was prepared. 50 µl of the prepared cell suspension was added to each well. Cells were allowed to adhere for 20 minutes before adding 150 µl of incubation medium. The plate was then incubated overnight. Cell networking structures were examined under a microscope and pictures were taken at 10× using image J. Total length of the network per picture was evaluated and divided by the results obtained for conditioned medium obtained form the patient's initial PBMCs to obtain the relative tube length. For negative control EBM (Lonza, CC3121) supplemented with 10% FCS and 1% P/S was used. For a positive control, the EGM bullet kit was used (Lonza, CC3124). The total length of capillary-like tubes showed a 1.9±0.2 increase when normalized to control PBMCs (FIGS. 6A and 6B).

The osteogenic potential of the CD31+ enriched cell population was also confirmed by Alizarin red staining. Mesenchymal stromal cells were purchased from the company ATCC (ATCC-PCS-500-012). Cells from passage 3-4 were utilized for the experiments. In brief, $2.4 \times 10^4$ cells per well were seeded in a 96 well-plate and cultivated in expansion medium for 24 hours before induction. Osteogenic differentiation medium was purchased commercially (LifeTechnologies, A10072-01) and diluted 1:1 with sterile filtered conditioned media and 100 µl medium were applied to each well with a medium exchange twice a week. Conditioned medium was derived from purified PBMCs, CD31+ and CD31− that were cultivated in DMEM low Glucose (Sigma-Aldrich) supplemented with 10% fetal calf serum (Biochrome), 1% Glutamax (LifeTechnologies) and 1% penicillin/streptomycin (Biochrome). $1.2 \times 10^6$ cells were kept in 6 ml of medium over 24 hours. The medium was then sterile filtered and stored at −20° C. until further experiments. At the end of the differentiation procedure the cell number was determined using a redox-based metabolic assay (AlamarBlue Cell Viability Reagent, LifeTechnologies), before the osteogenic differentiation was visualized via Alizarin Red S staining (ARS). Mineralized matrix positively stained for ARS was rinsed repeatedly with $H_2O$ before matrix-bound ARS was dissolved by addition of 10% cetylpyridinium chloride and colorimetrically detected at 562 nm. The resulting values were normalized to the metabolic rate and related to the control cell group that was cultured in regular osteogenic differentiation medium. Calcification was increased by 1.8±0.3 compared to control MSCs (FIGS. 6C and 6D). These data demonstrate that the CD31+ enriched cell population retained their angiogenic and osteogenic potential. Accordingly, these cells can be used to support angiogenesis and osteogenesis.

Example 5

Tissue Waste as a Source for CD31+ Cell Enrichment

Accessing bone fracture location requires suction of blood coming from injured soft tissues within the vicinity of the bone fracture. These blood and tissue samples are currently considered a medical waster product. However, cells with a high regenerative potential may be contained in these soft tissues. The suction waste was collected postoperatively (FIG. 7). Liquid and tissue were separated using a 100 µm cell strainer. For the tissue sample, gentle MACS dissociator was used before additional filtering. For the liquid sample, a density centrifugation step was performed to obtain peripheral blood mononuclear cells (PBMCs). Subsequently, red blood cell lysis was performed for 15 min on ice.

The composition of the liquid and tissue samples was analyzed with regards to CD31+ cell composition. Specifically, cells were stained for the presence of specific cell surface markers, e.g., CD14, CD45, CD31, CD3, and CD19, for CD31+ cells, and analyzed by flow cytometry. An initial gating on PBMCs was performed using FSC and SSC parameters.

As shown in FIG. 8, the composition of the CD31+ fraction within the tissue and liquid samples differs from the one observed in peripheral blood samples as shown in FIG. 5B. However, cells that are critical to angiogenesis and osteogenesis, for example, monocytes, were observed within the CD31+ fraction, suggesting that the medical waste product could be used as a source of CD31+ cells. The tissue sample had a higher CD31+ monocyte population (34%) when compared to the liquid sample (12%). Consequently, this sample may be beneficial for osteogenesis and, thus, be beneficial for bone healing.

The levels of CD45+ cells (leukocytes) within the tissue and liquid samples were quantified according to antibody staining and FACS analysis. Briefly, tissue and liquid samples were prepared and stained for the presence of the specific marker, CD45, to identify leukocytes, and then quantified by flow cytometry analysis. As shown in FIG. 9, about 70% of the total cell population within the tissue sample were CD45+ leukocytes, and more than 90% of cells were identified as CD45+ cells from the liquid sample.

Subsequently, the level of CD31+ cells within the leukocyte population was determined according to antibody staining and FACS analysis. FIG. 10 demonstrated the initial CD31+ levels among leukocytes within the tissue and liquid samples. About 60-70% of leukocytes within the tissue and liquid samples were CD31+ cells, suggesting that leukocytes within the tissue and liquid samples were a great source of CD31+ cells, and these CD31+ cells may be further enriched using the devices described herein.

These results demonstrated that the blood and soft tissues at the site of bone fracture can be utilized as a source of CD31+ cells, and CD31+ cells from these samples can be further enriched using the devices described herein.

Discussion

A cell sorting strategy that would allow for enrichment of beneficial cells from whole blood was evaluated. This approach for positive cell isolation provides a clean (bead free) cell population enriched for a specified cell surface marker, e.g.,. CD31+ cells.

The commercial aptamer showed high sensitivity and specificity for CD31+ cells derived from PBMCs. Flow cytometry data showed mainly double positive (CD31+ and Aptamer+) and double negative populations (CD31- and Aptamer-) for cells isolated using aptamer concentrations of 2 µg/ml and above. Also, magnetic isolation bead separation resulted in similar enrichment for aptamer and antibody based isolation.

Cell release from aptamer-coupled beads was mediated solely by mechanical forces and did not require the use of any additional chemicals that could contaminate the isolated cells. The aptamer concentration, bead number and combining uncoated and aptamer coated beads were adjusted to reach an optimized cell yield, CD31+ purity, and cell viability.

In current commercial approaches, cell release from beads coupled to an antibody utilizes an elution buffer, and antibodies remain attached to the cells. Aptamer-based strategies reported to date typically require exposure to the aptamer complementary strand, enzymatic treatment (Shen et al., *Advanced materials.* 2013;25: 2368-2373), or use of a high concentration dextran sulfate (Yoon et al., *PLoS ONE.* 2015;10: e0131785-19). Chemical-free approaches to aptamer binding have been reported in which the temperature and shear sensitivity of aptamer binding has been exploited in microfluidic devices (Zhu et al., *Lab Chip.* 2012; 12(18): 3504-351; Lin et al., *IET Nanobiotechnology.* ieee; 2014;8).

This is the first report of reversible aptamer binding without the use of any chemical or temperature modification. Shear stresses induced by resuspending the beads can be sufficient to induce cell release. Additionally, by resuspending the beads and separating them, there is a loss of the avidity effect coming from multiple beads in contact with the cells and the affinity of individual aptamer might be too weak to hold the cells for long. As some cells still remained attached to the beads after shearing, as evidenced by their recovery with a subsequent DNAse step, higher shear stresses could potentially release a greater number of CD31+ cells from the agarose beads. However, increased shear could also lead to cell damage and loss of cell viability. The aptamer affinity was reported to be significantly lower ($Kd=1.14 \times 10^{-9}$ M) than the extremely high affinity biotin-neutravidin linkage ($Kd=10^{-14}$ M). Therefore, bead-free cells were also aptamer-free.

Importantly, the released cell population described herein is free of beads, likely due to the size difference between the beads and the mesh size of the filter component. Neutravidin agarose beads, with a diameter initially between 45 and 165 µm, were filtered through a 100 µm cell strainer to select only larger size beads. Concerns from regulatory offices often relate to the possibility of remaining beads in the final product, since most of the cell sorting options currently available rely on beads in the nanometer to micrometer range. However, the filters at the base of the tubes exemplified herein had a 20 µm mesh size that prevented bead passage, but was still adequate for leukocytes, since their diameter is between 6 and 10 µm (Schmid-Schönbein et al., *Blood.* 1980;56: 866-875; Downey et al., *J Appl Physiol.* 1990;69: 1767-1778). The possibility of phagocytosis of immunobeads during positive cell isolation is also a major concern (Burkardt 0, et al., *Annals of anatomy.* 2015; 184(1):55-60), but is not an issue in embodiments set forth herein in which the beads used are several times larger than the cells creating a clear size separation between cell and capturing beads.

Use of an embodiment of the devices exemplified herein produced an enriched CD31+ cell population with increased angiogenic and osteogenic potential. A particular enrichment in monocytes was noted since they had the highest level of CD31 expression among PBMCs. The conditioned medium from the cell population enriched with this system led to an increase in the total tube network length in an angiogenesis assay, and enhanced the osteodifferentiation of MSCs. However, angiogenic and osteogenic promotion are not exclusive to monocytes among CD31+ cells, and the enrichment of naïve T cells may also underlie these effects. Indeed, upon stimulation, CD31+ T cells had an increased secretion of angiogenic factors compared to CD31- T and those cytokines are highly involved in vessel development and damage response to tissue ischemia (Kushner et al, *Blood cells, molecules & diseases;* 2009;44: 74-78).

The devices described herein have significant therapeutic potential. It is commonly accepted that $10^6$ PBMCs/ml can be isolated from blood (Nilsson et al., *Clinical and Vaccine Immunology.* 2008;15: 585-589). This would imply that with the current approach, approximately 15.8 million enriched CD31+ cells could be collected from 100 ml of blood, which is a reasonable blood draw. The devices of the present invention can also be utilized to target other surface antigens for enrichment. Methods to generate an aptamer to any target of interest have been previously reported (see, e.g., Guo et al, *Int J Mol Sci.* 2008; 9(4): 668-678), and allow for the in vitro evolution of nucleic acid molecules with highly specific binding to target molecules.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

We claim:

1. A system for enriching cells with a CD31 cell surface marker, comprising:
   an anti-CD31 aptamer suitable for specifically binding the CD31 cell surface marker;
   beads coupled to the aptamer having a diameter of about 30-200 μm;
   wherein the aptamer is coupled to the beads in a manner that allows for release of the cells in the absence of a chemical agent, and production of a cell population enriched for cells with the CD31 cell surface marker substantially free of beads and aptamer; and
   beads having a diameter of about 30-200 μm that are not coupled to the aptamere,
   wherein the beads coupled to the aptamer and the beads not coupled to the aptamer are present in a ratio of about 1:1 to about 3:1, wherein the system comprises a structure containing the beads coupled to the aptamer nd the beads not coupled to the aptamer.

2. The system of claim 1, wherein the aptamer is non-covalently coupled to the beads.

3. The system of claim 1, wherein the beads are agarose beads.

4. The system of claim 1, wherein the aptamer is present at a concentration of about 1-20 µg/mL of beads; or wherein the aptamer is present at a concentration of about 5 µg/mL of beads.

5. A method of enriching cells with a CD31 cell surface marker in a cell population, comprising:
providing the system of claim 1;
contacting the aptamer-coupled beads with the cell population containing cells with and without the CD31 cell surface marker;
washing the aptamer-coupled beads with a wash buffer such that all or a portion of the cells without the CD31 cell surface marker are removed from the cell sample;
subjecting the aptamer-coupled beads to a mechanical force sufficient to release the cells with the CD31 cell surface marker from the aptamer-coupled beads; and
recovering the cells with the CD31 cell surface marker from the aptamer-coupled beads;
thereby producing a cell population that is enriched in cells with the CD31 cell surface marker and is substantially free of beads and/or aptamer.

6. The method of claim 5, wherein the mechanical force is applied by resuspension of the aptamer-coupled beads in a resuspension buffer, wherein the resuspension buffer does not contain an agent capable of releasing the cells with the CD31 cell surface marker from the aptamer-coupled beads.

7. The method of claim 5, wherein the cells with the CD31 cell surface marker are recovered from the aptamer-coupled beads by passage through a filter having a pore size of less than 30 µm.

8. The method of claim 5, wherein the beads are not magnetic.

9. The method of claim 5, wherein the cell population is isolated from a blood sample, a bone marrow sample, a hematoma sample, a tissue sample collected at the site of a bone fracture, a fluid sample collected at the site of a bone fracture, or combinations thereof; wherein the cell population is isolated from a peripheral blood mononuclear cell (PBMC) sample; wherein or the cell population is isolated from a tissue sample collected at the site of a bone fracture or a fluid sample collected at the site of a bone fracture.

10. The method of claim 5, further comprising obtaining the cell population from a subject.

11. The method of claim 5, further comprising administering the cell population enriched for cells with the CD31 cell surface marker to a subject.

12. A method of promoting angiogenesis and/or osteogenesis at a surgical site in a subject, comprising:
obtaining a cell sample from the subject, wherein the cell sample contains CD31+ and CD31− cells;
contacting the cell sample with the system of claim 1, wherein the aptamer is suitable for specifically binding CD31;
washing the aptamer-coupled beads with a wash buffer such that all or a portion of the CD31− cells are removed from the cell sample;
subjecting the aptamer-coupled beads to a mechanical force sufficient to release the CD31+ cells from the aptamer-coupled beads;
recovering the CD31+ cells from the aptamer-coupled beads; such that the recovered CD31+ cells are substantially free of beads and/or aptamer; and
introducing the recovered CD31+ cells at the surgical site in the subject.

13. The system of claim 1, wherein the structure comprises a column and the beads coupled to the aptamer and the beads not coupled to the aptamer are packed in the column.

14. The system of claim 13, further comprising a filter having a pore size smaller than the diameter of the beads.

15. The system of claim 13, wherein the column is sized to fit inside a centrifuge tube.

16. The system of claim 13, wherein the column is fitted with a syringe.

17. the system of claim 1, wherein the aptamer is covalently coupled to the beads.

18. The system of claim 1, wherein the beads are not magnetic.

19. The system of claim 1, wherein the beads have a diameter of about 50-150 µm.

20. The system of claim 1, wherein the beads have a diameter of about 100-150 µm.

21. The system of claim 1, wherein the chemical agent is selected from the group consisting of a nuclease, a protease, a nucleic acid complementary to the aptamer, and an antibody specific for the cell surface marker, and combinations thereof.

22. The method of claim 5, wherein the cells are mammalian cells.

23. The method of claim 22, wherein the mammalian cells are non-human cells.

24. The method of claim 22, wherein the mammalian cells are human cells.

25. The method of claim 6, wherein the agent is selected from the group consisting of a nuclease, a protease, a nucleic acid complementary to the aptamer, and an antibody specific for the cell surface marker, and combinations thereof.

26. The method of claim 10, wherein the subject is a non-human subject.

27. The method of claim 10, wherein the subject is a human subject.

28. The method of claim 12, wherein the subject is a non-human subject.

29. The method of claim 12, wherein the subject is a human subject.

* * * * *

UNITED STATES PATENT AND TRADEMARK OFFICE
CERTIFICATE OF CORRECTION

PATENT NO. : 10,758,573 B2  
APPLICATION NO. : 15/580710  
DATED : September 1, 2020  
INVENTOR(S) : Pascal Joly et al.

Page 1 of 1

It is certified that error appears in the above-identified patent and that said Letters Patent is hereby corrected as shown below:

In the Claims

At Column 52, Line 61, Claim number 1, delete "aptamere" and replace it with -- aptamer --

At Column 52, Lines 67, Claim number 1, delete "nd" and replace it with -- and --

Signed and Sealed this  
Eighth Day of December, 2020

Andrei Iancu  
*Director of the United States Patent and Trademark Office*

SEQUENCE LISTING

```
<160> NUMBER OF SEQ ID NOS: 2

<210> SEQ ID NO 1
<211> LENGTH: 6831
<212> TYPE: DNA
<213> ORGANISM: Homo sapiens
<220> FEATURE:
<221> NAME/KEY: misc_feature
<223> OTHER INFORMATION: Homo sapiens platelet/endothelial cell adhesion
      molecule 1 (PECAM1), mRNA
```

<400> SEQUENCE: 1

```
ccaggcccca ttgttcccgg tttccagcca tggctgccat tacctgacca gcgccacagc    60
cggtctctct gcaggcgccg ggagaagtga ccagagcaat ttctgctttt cacagggcgg   120
gtttctcaac ggtgacttgt gggcagtgcc ttctgctgag cgagtcatgg cccgaaggca   180
gaactaactg tgcctgcagt cttcactctc aggatgcagc cgaggtgggc ccaaggggcc   240
acgatgtggc ttggagtcct gctgaccctt ctgctctgtt caagccttga gggtcaagaa   300
aactctttca caatcaacag tgttgacatg aagagcctgc cggactggac ggtgcaaaat   360
gggaagaacc tgaccctgca gtgcttcgcg gatgtcagca ccacctctca cgtcaagcct   420
cagcaccaga tgctgttcta taaggatgac gtgctgtttt acaacatctc ctccatgaag   480
agcacagaga gttatttat tcctgaagtc cggatctatg actcagggac atataaatgt   540
actgtgattg tgaacaacaa agagaaaacc actgcagagt accaggtgtt ggtggaagga   600
gtgcccagtc ccagggtgac actggacaag aaagaggcca tccaaggtgg gatcgtgagg   660
gtcaactgtt ctgtcccaga ggaaaaggcc ccaatacact tcacaattga aaaacttgaa   720
ctaaatgaaa aaatggtcaa gctgaaagga gagaagaatt ctcgagacca gaattttgtg   780
atactggaat tccccgttga ggaacaggac cgcgttttat ccttccgatg tcaagctagg   840
atcatttctg ggatccatat gcagacctca gaatctacca agagtgaact ggtcaccgtg   900
acggaatcct tctctacacc caagttccac atcagcccca ccggaatgat catggaagga   960
gctcagctcc acattaagtg caccattcaa gtgactcacc tggccaggga gtttccagaa  1020
atcataattc agaaggacaa ggcgattgtg cccacaacag acatggcaa caaggctgtg  1080
tactcagtca tggccatggt ggagcacagt ggcaactaca cgtgcaaagt ggagtccagc  1140
cgcatatcca aggtcagcag catcgtggtc aacataacag aactattttc caagcccgaa  1200
ctggaatctt ccttcacaca tctgaccaa ggtgaaagac tgaacctgtc ctgctccatc  1260
ccaggagcac ctccagccaa cttcaccatc cagaaggaag atacgattgt gtcacagact  1320
caagatttca ccaagatagc ctcaaagtcg gacagtggga cgtatatctg cactgcaggt  1380
attgacaaag tggtcaagaa aagcaacaca gtccagatag tcgtatgtga aatgctctcc  1440
cagcccagga tttcttatga tgcccagttt gaggtcataa aaggacagac catcgaagtc  1500
cgttgcgaat cgatcagtgg aactttgcct atttcttacc aacttttaaa aacaagtaaa  1560
gttttggaga atagtaccaa gaactcaaat gatcctgcgg tattcaaaga caccccact  1620
gaagacgtcg aataccagtg tgttgcagat aattgccatt cccatgccaa atgttaagt  1680
gaggttctga gggtgaaggt gatagccccg gtggatgagg tccagatttc tatcctgtca  1740
agtaaggtgg tggagtctgg agaggacatt gtgctgcaat gtgctgtgaa tgaaggatct  1800
ggtcccatca cctataagtt ttacagagaa aaagagggca aaccccttct cacaaatgacc  1860
tcaaatgcca cccaggcatt ttggaccaag cagaaggcta gcaaggaaca ggagggagag  1920
tattactgca cagccttcaa cagagccaac cacgcctcca gtgtccccag aagcaaaata  1980
ctgacagtca gagtcattct tgccccatgg aagaaaggac ttattgcagt ggttatcatc  2040
ggagtgatca ttgctctctt gatcattgcg gccaatgtt attttctgag gaaagccaag  2100
gccaagcaga tgccagtgga atgtccagg ccagcagtac cacttctgaa ctccaacaac  2160
gagaaaatgt cagatcccaa tatggaagct aacagtcatt acggtcacaa tgacgatgtc  2220
agaaaccatg caatgaaacc aataaatgat aataagagc ctctgaactc agacgtgcag  2280
```

```
tacacggaag ttcaagtgtc ctcagctgag tctcacaaag atctaggaaa gaaggacaca    2340
gagacagtgt acagtgaagt ccggaaagct gtccctgatg ccgtggaaag cagatactct    2400
agaacggaag gctcccttga tggaacttag acagcaaggc cagatgcaca tccctggaag    2460
gacatccatg ttccgagaag aacagataat ccctgtattt caagacctct gtgcacttat    2520
ttatgaacct gccctgctcc cacagaacac agcaattcct caggctaagc tgccggttct    2580
taaatccatc ctgctaagtt aatgttgggt agaaagagat acagagggc tgttgaattt     2640 cccacatacc ctccttccac caagttggaa catccttgga aattggaaga gcacaagagg    2700
agatccaggg caaggccatt gggatattct gaaacttgaa tattttgttt tgtgcagaga    2760
taaagacctt ttccatgcac cctcatacac agaaaccaat tttcttttt atactcaatc     2820 atttctagcg catggcctgg ttagaggctg gttttttctc ttttcctttg gtccttcaaa    2880
ggcttgtagt tttggctagt ccttgttctt tggaaataca cagtgctgac cagacagcct    2940 cccctgtcc cctctatgac ctcgccctca caaatggga aaaccagact acttgggagc      3000
accgcctgtg aaataccaac ctgaagacac cgttcattca ggcaacgcac aaaacagaaa    3060
atgaaggtgg aacaagcaca gatgttcttc aactgttttt gtctacactc tttctctttt    3120
cctctaccat gctgaaggct gaaagacagg aagatggtgc catcagcaaa tattattctt    3180
aattgaaaac ttgaaatgtg tatgtttctt actaattttt aaaaatgtat tccttgccag    3240
ggcaggcaag gtggctcacg cctgtaatcc cagcacttca ggaggctgag gtgggcggat    3300
cacctgaggt caggagtttg agaccagcct gatgaaaccc tgtctctact aaaaatacaa    3360
gaattagccg ggcgtggtgg cgcatgcctg tagtatcagc tactcaagag gctgaggtga    3420
gattatcgct tgaacccagg aaacggaggt tgtagtgagc ggagatcgcg ccactgcact    3480
ccagcctgag tgacagagtg agaatccatc tcaaaaaaaa caaaaaacaa aattgcttgc    3540
taaagaagtg gtctcctgag gtcttaagac attcctgaca gtgtcttgag tgggtgggag    3600
agaggctgct gtcattgcgc tgtggaattt cacagatgag aaccacgcct agccaaaatc    3660
acttttcctg tttgcctcag tgacacagct gcagggaccc tcgtggatgt tgtattaaat    3720
aaatttgacc tttgctcttt gcagatctgt gaaatgttgt cttctgaggg gccacatgca    3780
tctatagtgc tgaggactcc ttgggcctct gaagtcacag agagaaccga gcaggtctat    3840 gttttttgttt tgttgttttg agacggagat tcgctcttgt tgcccgggct ggactgcagc    3900
ggcgcaacct ctgctcactg caacctccgc ctcctgggtt caagcagttc tcctgtctca    3960
gcctcccgag tagctgggat tacaggcaca tgtcaccacg cctggctaat ttttgtattt    4020
ttagtagaga tgggggttca ccacgttggc caggctgatc tcgaatgcct gacctttggt    4080
gatctgcccg ccttgtcctc atgtgtgctc cacaggcctt tgggttggga ttgcaggcgt    4140
gagccaccat gcccagccta gactcttttg acaatatgat gaaagctgtt ggttcctttc    4200
cccaacacac acacaccgag ttgtatcacg aaaatgtcat acaatttcca ggttttctga    4260
gtggtgggct cagattgagg tcaaaggatc agacgacctc taacgacctt catgtctctg    4320
ttgatgatct ggggacagcc agatcccctg tgtccaggga gttccttagt cccttgccac    4380
caccagagaa gggcaattgc cacgggagct gcaaagaccc tattcctact cctggtgcct    4440
tacttatgca gcacgactga attttttgtt ttgttttgtt ttgttgagac agggcttgc     4500 tctgttgccc aggctggagt gcagtggcac aacaatggct caccgcagcc tcgaacccct    4560
gggctcaagc gatcctccca tctcagcttc ctgggtagct gggaccagag gcgtgagccg    4620
ccatagctgg ctaatttttta atttttttttt tgcagagatg aggtttcacc atggtgccca    4680
```

```
ggctggtctc gaacttctgg gctcaagtga tcctccctcc ttggcctcgc aaagtgctgg    4740
gattgcaggc atgagccacc gccccggcc tgtggagcac acatgagttt aaaattactt     4800
tcccttctgc ctatatttcc gaggaggaaa cttcatgcgc agggatcttt cttagtggat    4860
ttaatggcta aaaggtctgt ctgaatccag gacgctggct ttagccttcc tcggcagctg    4920
ccgtaacccc ggtgtctaaa cctgaagcat cccaggagca cccactccag gagttttctc    4980
ggccgcggaa ctcattagtt agagcgccct cttgtgttct catgtggtaa tcggtcactg    5040
aaggacttaa aatggtcctt agccaacaca cagtaaaact tttccctctt ctgaccccaa    5100
gaggtcagcc acccatttca tgagcatata ctggtcgccc catcagcgtt ctctgattgg    5160
ctaactgaac ccactccccg acctagactc aagacaggcg aagtgacgct taggtcaaca    5220
ttcactcact aaagcaacga ctgtcgggcg atttttgtctc ccgctggttt tggaatggtg    5280
tctggagaca ttttttggttg tcacagctgg gtgggtgtgc tcccggcatc tggtgggtag    5340
aaaccaagca tgctcctaaa catcctacag gcacagaacc gtctcccacg accaagcatg    5400
atcaagtccc aaatgccaat aatggccagg ttgagaaact ctgcacagaa gcatccagtt    5460
atttgtctgt ttgctcaaca agcttgtgct catcatgctc tgtgttcctg acgctgtgct    5520
gggtgttggc ggtgggaaga ttacaagagt cacatggcag ctgtcctcct ggaaggtaca    5580
acccagtaga gatgcagact aacagagagc caattacaaa gcagtgtgac aagcgtcatg    5640
gtggaaaatt aaaagctcaa acaagggcac atgggagggg cttccaacac agactttggg    5700
ggatccagga aggtctaaga ggaaagtggg tctcaccaaa gccttgacca taggcagagg    5760
gtaccagtgg aaaaggtggg gtgaagaaca ttgaggacaa aaggaagaag tgcaggaagg    5820
ccctgaggca agggagtggg gggtgccctg gagggatggc agcagggcag tctgtcagac    5880
ccaagtggcc tccagcccta gaagccaatt agtcctcctc aaaaagctgt cactgtcccc    5940
taagaattgc tgccaggctc ccactggcct gactcagtct ttgagagtct taaggaggag    6000
gtctctgaaa ggtacacacc aagaactctc cccagcacag ctgtttttaa gactctccac    6060
cagcgtcatt ggcgtgttgg gaagaaaccc tctgccacag aggccagctt cagccttttgc    6120 ctaacaccgc aagggcaaat ggaaaggtaa acgggaagga gatgtctccc cagcaggcta    6180
tttgaggaca gtcttccctg cagaagatct caacctgggg tccacagagt ggaaatgtta    6240
gagtagggag ctaggcaaac atgagcagga caggtgaggg cccccacagg aatgtcaggc    6300
taccatcagg tgatggtcag gtggttgtta aactgtctct gtaaaataat aattggttgc    6360
agccagctcc aagcaaggac agtctctcaa tagatacaaa acaccctgat ctggtgatca    6420
gccgcttccc gataagatct caggagctgg gcaagcagcc tggagcatgc gcaccaagag    6480
gcaaaatggc ggaatttaac cagtatatga cctaccttcc tctgggaacg cacgactggt    6540
aaggggaaaa atgcctcaag tgagcatgcg cgcaacttca gtaatcacac tgtgcatgcg    6600
accccttcca agtgctggca ggtcaccaca tacgcggaca gcctgctgca agggaagaat    6660
caggggagat gagacgtaaa tcccagaact atgccaaata cataaaaccc caagttaagg    6720
gtcaggcagg gcacttagat ctctcaagtt gcctgcctga cccaagtgta gtgtacttcc    6780
ttttgttcct gctctaaaac ttttaataa actctcactc ctgctctaaa a              6831
```

<210> SEQ ID NO 2
<211> LENGTH: 737
<212> TYPE: PRT
<213> ORGANISM: Homo sapiens
<220> FEATURE:

<221> NAME/KEY: misc_feature
<223> OTHER INFORMATION: Platelet endothelial cell adhesion molecule
     precursor

<400> SEQUENCE: 2

```
Met Gln Pro Arg Trp Ala Gln Gly Ala Thr Met Trp Leu Val Leu
1               5                   10                  15

Leu Thr Leu Leu Leu Cys Ser Ser Leu Glu Gly Gln Glu Asn Ser Phe
            20                  25                  30

Thr Ile Asn Ser Val Asp Met Lys Ser Leu Pro Asp Trp Thr Val Gln
        35                  40                  45

Asn Gly Lys Asn Leu Thr Leu Gln Cys Phe Ala Asp Val Ser Thr Thr
    50                  55                  60

Ser His Val Lys Pro Gln His Gln Met Leu Phe Tyr Lys Asp Asp Val
65                  70                  75                  80

Leu Phe Tyr Asn Ile Ser Ser Met Lys Ser Thr Glu Ser Tyr Phe Ile
                85                  90                  95

Pro Glu Val Arg Ile Tyr Asp Ser Gly Thr Tyr Lys Cys Thr Val Ile
            100                 105                 110

Val Asn Asn Lys Glu Lys Thr Thr Ala Glu Tyr Gln Val Leu Val Glu
        115                 120                 125

Gly Val Pro Ser Pro Arg Val Thr Leu Asp Lys Lys Glu Ala Ile Gln
    130                 135                 140

Gly Gly Ile Val Arg Val Asn Cys Ser Val Pro Glu Glu Lys Ala Pro
145                 150                 155                 160

Ile His Phe Thr Ile Glu Lys Leu Glu Leu Asn Glu Lys Met Val Lys
                165                 170                 175

Leu Lys Arg Glu Lys Asn Ser Arg Asp Gln Asn Phe Val Ile Leu Glu
            180                 185                 190

Phe Pro Val Glu Glu Gln Asp Arg Val Leu Ser Phe Arg Cys Gln Ala
        195                 200                 205

Arg Ile Ile Ser Gly Ile His Met Gln Thr Ser Glu Ser Thr Lys Ser
    210                 215                 220

Glu Leu Val Thr Val Thr Glu Ser Phe Ser Thr Pro Lys Phe His Ile
225                 230                 235                 240

Ser Pro Thr Gly Met Ile Met Glu Gly Ala Gln Leu His Ile Lys Cys
                245                 250                 255

Thr Ile Gln Val Thr His Leu Ala Gln Glu Phe Pro Glu Ile Ile Ile
            260                 265                 270

Gln Lys Asp Lys Ala Ile Val Ala His Asn Arg His Gly Asn Lys Ala
        275                 280                 285

Val Tyr Ser Val Met Ala Met Val Glu His Ser Gly Asn Tyr Thr Cys
    290                 295                 300

Lys Val Glu Ser Ser Arg Ile Ser Lys Val Ser Ser Ile Val Val Asn
305                 310                 315                 320

Ile Thr Glu Leu Phe Ser Lys Pro Glu Leu Glu Ser Ser Phe Thr His
                325                 330                 335

Leu Asp Gln Gly Glu Arg Leu Asn Leu Ser Cys Ser Ile Pro Gly Ala
            340                 345                 350

Pro Pro Ala Asn Phe Thr Ile Gln Lys Glu Asp Thr Ile Val Ser Gln
        355                 360                 365

Thr Gln Asp Phe Thr Lys Ile Ala Ser Lys Ser Asp Ser Gly Thr Tyr
    370                 375                 380

Ile Cys Thr Ala Gly Ile Asp Lys Val Val Lys Lys Ser Asn Thr Val
```

-continued

```
                385                 390                 395                 400
        Gln Ile Val Val Cys Glu Met Leu Ser Gln Pro Arg Ile Ser Tyr Asp
                            405                 410                 415

Ala Gln Phe Glu Val Ile Lys Gly Gln Thr Ile Glu Val Arg Cys Glu
                            420                 425                 430

Ser Ile Ser Gly Thr Leu Pro Ile Ser Tyr Gln Leu Leu Lys Thr Ser
                            435                 440                 445

Lys Val Leu Glu Asn Ser Thr Lys Asn Ser Asp Pro Ala Val Phe
                    450                 455                 460

Lys Asp Asn Pro Thr Glu Asp Val Glu Tyr Gln Cys Val Ala Asp Asn
        465                 470                 475                 480

Cys His Ser His Ala Lys Met Leu Ser Glu Val Leu Arg Val Lys Val
                            485                 490                 495

Ile Ala Pro Val Asp Glu Val Gln Ile Ser Ile Leu Ser Ser Lys Val
                            500                 505                 510

Val Glu Ser Gly Glu Asp Ile Val Leu Gln Cys Ala Val Asn Glu Gly
                            515                 520                 525

Ser Gly Pro Ile Thr Tyr Lys Phe Tyr Arg Glu Lys Glu Gly Lys Pro
                    530                 535                 540

Phe Tyr Gln Met Thr Ser Asn Ala Thr Gln Ala Phe Trp Thr Lys Gln
        545                 550                 555                 560

Lys Ala Ser Lys Glu Gln Glu Gly Glu Tyr Tyr Cys Thr Ala Phe Asn
                            565                 570                 575

Arg Ala Asn His Ala Ser Ser Val Pro Arg Ser Lys Ile Leu Thr Val
                            580                 585                 590

Arg Val Ile Leu Ala Pro Trp Lys Lys Gly Leu Ile Ala Val Val Ile
                    595                 600                 605

Ile Gly Val Ile Ile Ala Leu Leu Ile Ile Ala Ala Lys Cys Tyr Phe
                    610                 615                 620

Leu Arg Lys Ala Lys Ala Lys Gln Met Pro Val Glu Met Ser Arg Pro
        625                 630                 635                 640

Ala Val Pro Leu Leu Asn Ser Asn Asn Glu Lys Met Ser Asp Pro Asn
                            645                 650                 655

Met Glu Ala Asn Ser His Tyr Gly His Asn Asp Asp Val Arg Asn His
                            660                 665                 670

Ala Met Lys Pro Ile Asn Asp Asn Lys Glu Pro Leu Asn Ser Asp Val
                            675                 680                 685

Gln Tyr Thr Glu Val Gln Val Ser Ser Ala Glu Ser His Lys Asp Leu
                            690                 695                 700

Gly Lys Lys Asp Thr Glu Thr Val Tyr Ser Glu Val Arg Lys Ala Pro
        705                 710                 715                 720

Asp Ala Val Glu Ser Arg Tyr Ser Arg Thr Glu Gly Ser Leu Asp Gly
                            725                 730                 735

Thr
```